(12) United States Patent
Margines

(10) Patent No.: US 9,064,274 B2
(45) Date of Patent: Jun. 23, 2015

(54) SYSTEMS AND METHODS OF PROCESSING PERSONALITY INFORMATION

(76) Inventor: Edward Y. Margines, Santa Ana, CA (US)

( * ) Notice: Subject to any disclaimer, the term of this patent is extended or adjusted under 35 U.S.C. 154(b) by 0 days.

(21) Appl. No.: 13/564,105

(22) Filed: Aug. 1, 2012

(65) Prior Publication Data
US 2013/0035912 A1 Feb. 7, 2013

Related U.S. Application Data

(60) Provisional application No. 61/515,047, filed on Aug. 4, 2011.

(51) Int. Cl.
*G06F 17/30* (2006.01)
*G06Q 30/02* (2012.01)

(52) U.S. Cl.
CPC ...... *G06Q 30/0276* (2013.01); *G06F 17/30867* (2013.01); *G06F 17/30864* (2013.01)

(58) Field of Classification Search
CPC .................... G06F 17/30864; G06F 17/30867
USPC .......................................... 707/758; 705/319
See application file for complete search history.

(56) References Cited

U.S. PATENT DOCUMENTS

| | | | | |
|---|---|---|---|---|
| 6,067,537 | A * | 5/2000 | O'Connor et al. | 706/47 |
| 6,401,094 | B1 * | 6/2002 | Stemp et al. | 1/1 |
| 7,454,357 | B2 | 11/2008 | Buckwalter et al. | |
| 7,890,581 | B2 * | 2/2011 | Rao et al. | 709/204 |
| 8,200,677 | B2 * | 6/2012 | Martino et al. | 707/749 |
| 8,234,346 | B2 * | 7/2012 | Rao et al. | 709/207 |
| 8,478,702 | B1 * | 7/2013 | Treiser | 706/12 |
| 8,549,061 | B2 * | 10/2013 | Rao et al. | 709/200 |
| 8,566,348 | B2 * | 10/2013 | Rinearson et al. | 707/769 |
| 2004/0210661 | A1 * | 10/2004 | Thompson | 709/228 |
| 2006/0122903 | A1 * | 6/2006 | Medrano et al. | 705/26 |

(Continued)

FOREIGN PATENT DOCUMENTS

WO    WO 0022558 A1 * 4/2000

OTHER PUBLICATIONS

International Search Report and Written Opinion dated Mar. 25, 2013, International Application No. PCT/US2012/049368, filed Aug. 2, 2012.

(Continued)

*Primary Examiner* — Pierre Vital
*Assistant Examiner* — Nargis Sultana
(74) *Attorney, Agent, or Firm* — Knobbe Martens Olson & Bear LLP

(57) ABSTRACT

A computer-based system and associated processes are disclosed for making personality-related recommendations to an entity. The system receives indications of one or more personality attributes of an entity. The system acquires indications of one or more personality attributes of a desired partner of the entity. The system applies a mathematical model to the one or more personality attributes of the entity and the one or more personality attributes of the desired partner of the entity. The mathematical model calculates one or more recommended changes to the personality attributes of the entity to increase a predicted relationship satisfaction score between the entity and the desired partner. The system selects a recommended action from a database of recommended actions, based at least in part on the recommended changes to the personality attributes of the entity. The system presents the recommended action.

18 Claims, 18 Drawing Sheets

(56) References Cited

U.S. PATENT DOCUMENTS

| | | | |
|---|---|---|---|
| 2007/0192106 A1* | 8/2007 | Zilca | 704/270 |
| 2008/0021794 A1* | 1/2008 | Vega | 705/26 |
| 2008/0147743 A1* | 6/2008 | Taylor et al. | 707/104.1 |
| 2010/0145869 A1* | 6/2010 | Brown | 705/319 |
| 2010/0324970 A1* | 12/2010 | Phelon et al. | 705/10 |
| 2011/0179116 A1* | 7/2011 | Solomon et al. | 709/204 |
| 2011/0283201 A1* | 11/2011 | Wachtel | 715/751 |
| 2012/0284080 A1* | 11/2012 | De Oliveira et al. | 705/7.29 |
| 2012/0290659 A1* | 11/2012 | Rao et al. | 709/204 |
| 2012/0330869 A1* | 12/2012 | Durham | 706/16 |
| 2013/0035912 A1* | 2/2013 | Margines | 703/2 |
| 2014/0019542 A1* | 1/2014 | Rao et al. | 709/204 |

OTHER PUBLICATIONS

Screenshots from http://www.youtube.com/watch?v=JW1uNICR0aY, video uploaded Aug. 20, 2010, screenshots taken Oct. 31, 2012.

International Preliminary Report of Patentability dated Apr. 3, 2014 for PCT Application No. PCT/US2012/049368 filed Aug. 2, 2012.

* cited by examiner

Self-survey of personality attributes

Please fill out the following survey:

― 401

Based on your survey results, we have calculated the following personality attributes:

Openness: 50% Adjust
Extraversion: 80% Adjust
Neuroticism: 30% Adjust
Conscientiousness: 60% Adjust
Agreeableness: 40% Adjust These will be stored in your user profile.

SYSTEMS AND METHODS OF PROCESSING PERSONALITY INFORMATION

CROSS-REFERENCE TO RELATED APPLICATIONS

This application claims priority to U.S. Pat. App. No. 61/515,047, filed Aug. 4, 2011, titled "SYSTEM AND METHOD FOR SOCIAL MATCHMAKING BASED ON PERSONALITY DATA." The aforementioned application is hereby incorporated by reference in its entirety as if set forth herein.

BACKGROUND

Matchmaking, the art of selecting partnerships among a body of people so that the selected partners will have an enjoyable and satisfactory relationship, is one of the oldest practices known to humankind. Traditionally, matchmaking has been done in various cultures by skilled individuals, by parents or relatives, or organically through relationships among the parties, such as through dating.

As time-honored as these traditions are, their difficulties and imperfections are well known. This is due in large part to the limited knowledge that the relevant parties bring: even the most skilled matchmakers must make decisions based on no more than a handful of past experiences and anecdotes of a handful more. Furthermore, the use of an external third party to dictate matches is in conflict with modern concepts of free choice and independence. Today, individuals not only want to know whether a relationship will work, but also what to do to improve a relationship's success, as can be easily seen through the proliferation of self-help books and magazines.

SUMMARY

Advances in mathematics, data analysis, and computer technology make possible automated predictions and recommendations that may be brought to bear in the area of matchmaking and relationship guidance. Disclosed herein are various systems and methods of processing personality information, to provide such useful outputs as recommendations for individuals, appropriate matches with potential partners, and other advice and insights. The outputs may be personally tailored to particular attributes of individuals through automatic computer analysis and the application of data models incorporating potentially vast quantities of historical and other input data. Additionally, modern technology enables the presentation of effective and accessible user interfaces where individuals may take advantage of the aforementioned data analysis, recommendations, guidance, and insights in a convenient and efficient manner.

Disclosed aspects include the generation and application of statistical, mathematical, and/or other models for assessing relationship satisfaction based on attributes, such as personality attributes. For example, metrics for two individuals relating to five personality attributes, namely openness, conscientiousness, extraversion, agreeableness and neuroticism, may be used to predict a likelihood of relationship satisfaction for either of the two individuals, through such models. The models may be implemented and operated through various computing devices and systems.

Such models may then be applied to produce practical and useful information, in various embodiments. One such useful application of these models is to generate recommendations for individuals as to how to improve their compatibilities with potential or hypothetical partners. For example, referring to the five attributes identified previously, an individual may provide personality attributes for that individual and a desired partner, and the models may be used to determine that the individual would have a more satisfactory relationship with that desired partner if the individual was more agreeable and less open. Further recommendations could then be made, for example relating to activities that would encourage such personality changes.

BRIEF DESCRIPTION OF THE DRAWINGS

FIG. 4 is a sample user interface of a survey for assessing personality attributes, as used in an embodiment.

DETAILED DESCRIPTION OF SPECIFIC EMBODIMENTS

Disclosed herein are systems and methods of processing attributes of entities. The entities may include an individual, an institution, or an object. Various embodiments disclosed herein are directed to problems of matching entities. Such matching may be used, for example, for identifying relationship partners among people, for matching business partners, for assigning students to schools, for assigning job-seekers to open positions, for selecting companies for mergers, for recommending products to individuals, and the like. Although the embodiments are described herein primarily in the context of matching male and female individuals into potential relationships, it will be understood that the systems and methods described herein may be applied to any of the aforementioned matching processes and/or other matching processes, and nonmatching processes.

In the various embodiments described herein, matching processes and/or other processes may be based on attributes associated with entities. The attributes may represent various qualities of the respective entities and may be provided by the respective entity, retrieved from an external source, and/or calculated by the various systems and methods described herein and/or by other systems and methods. Attributes may be numeric quantities and/or normumeric values, such as factors. In an embodiment, five factors relating to the personality of individuals are used, namely openness, conscientiousness, extraversion, agreeableness and neuroticism. In various embodiments, any subset of these personality traits may be used as attributes and/or other personality traits may be used as attributes. In various embodiments, nonpersonality traits, such as physical traits, personal information, location information, family information, and the like, may be included additionally or alternatively.

In the following disclosure, the terms "individual" and "partner" are used with respect to various embodiments, to refer to an entity about whom matching is sought, and an entity in a relationship or proposed for a relationship with the individual. It is understood that these terms and other terms may refer to any type of entity as described herein. Furthermore, various embodiments are described in which the individual submits requests for information relating to the individual and receives information relating to the individual. It will be understood that, in various additional embodiments, entities other than the individual may request information and/or receive information about the individual, for example where a professional matchmaker seeks potential partners on an individual's behalf.

Figure 1:
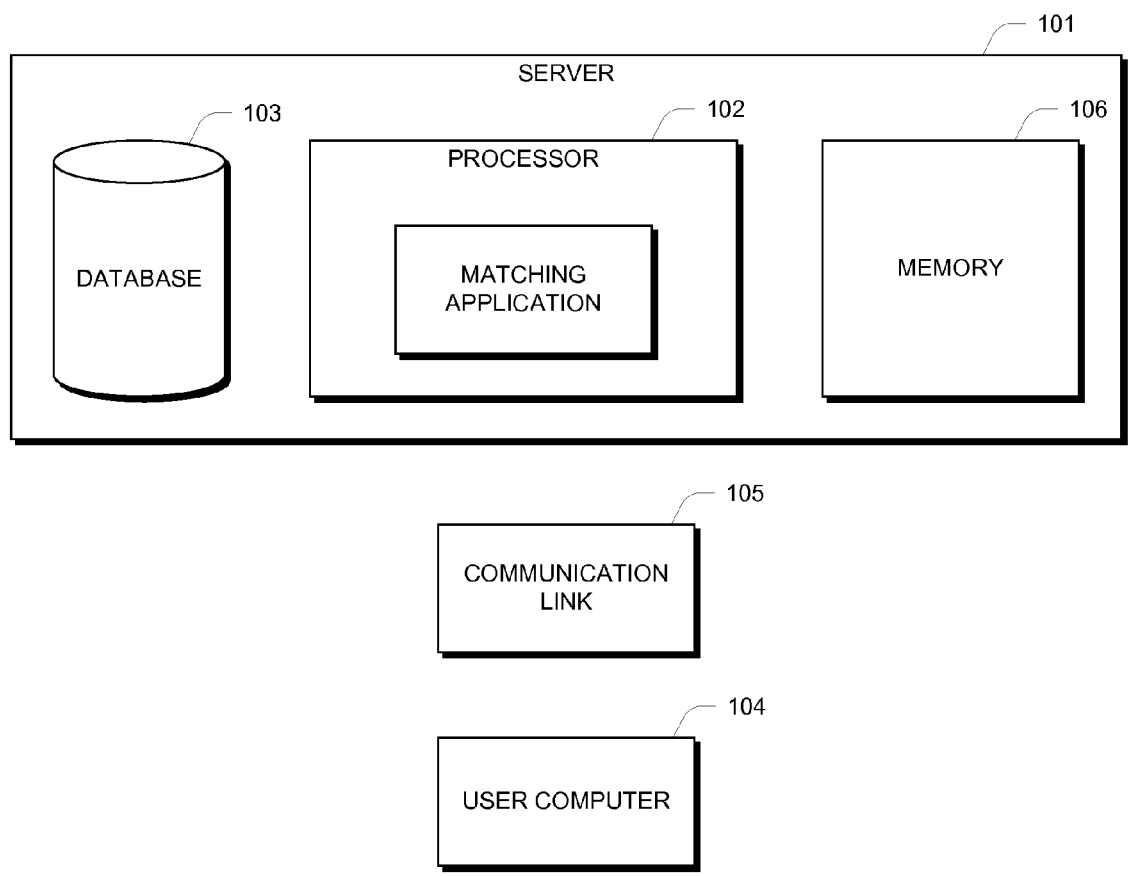
FIG. 1 is a block diagram of a server system, as used in an embodiment.

FIG. 1 is a block diagram of a server system, as used in an embodiment. In general, a server 101 comprising at least one processor 102, at least one database 103, and/or a memory 106, interacts with a user computer or computing device 104 via a communication link 105, such as the Internet. The server 101 may, in some embodiments, include multiple distinct computing devices (potentially in different geographic locations) that operate collectively as a server. In one embodiment, the server interacts with the user computing device 104 via a website, which can be hosted by the server 101 or another computer. In another embodiment, the server 101 interacts with the user computer 104 via a third-party social media platform. As another example, the server 101 can interact with the user computing device 104 via a smart phone application. Although a single user computing device is shown, the system is typically accessed by many user computing devices of many users.

In an embodiment, the user computing device 104 is a device that allows a user to interact with the web site. In one embodiment, the user computing device 104 is a conventional personal computer which is equipped with a conventional modem. In other embodiments, the user computing device can be a personal digital assistant, an interactive wireless communications device, such as a smart phone, an interactive television, a transponder, or the like.

Using the user computing device 104, a user can input user personality data. The user personality data can be in the form of the user's responses to a survey. The survey preferably includes a plurality of inquiries into matters which are relevant to an individual forming relationships with other people. Depending on the form of the inquiries, the user can provide numerical answers, true/false answers, or one or more selections from a list. The user can also provide word or narrative answers. These word or narrative answers can later be parsed for keywords or other relevant information, e.g., using the server. The user may provide the responses via a user interface displayed on the website, social media platform, smartphone application, etc. However, the user could also mail the responses to a system administrator, who may then enter the data on the user's behalf (e.g., via manual entry or a computer scanner).

The website or social media platform may include one or more computers. The computers comprise, by way of example, processors, program logic, or other substrate configurations representing data and instructions, which operate as described herein. In other embodiments, the processors can comprise controller circuitry, processor circuitry, processors, general purpose single-chip or multi-chip microprocessors, digital signal processors, embedded microprocessors, microcontrollers and the like.

The server may include, by way of example, processors, program logic, or other substrate configurations representing data and instructions, which operate as described herein. In other embodiments, the processors can comprise controller circuitry, processor circuitry, processors, general purpose single-chip or multi-chip microprocessors, digital signal processors, embedded microprocessors, microcontrollers and the like.

Figure 2:
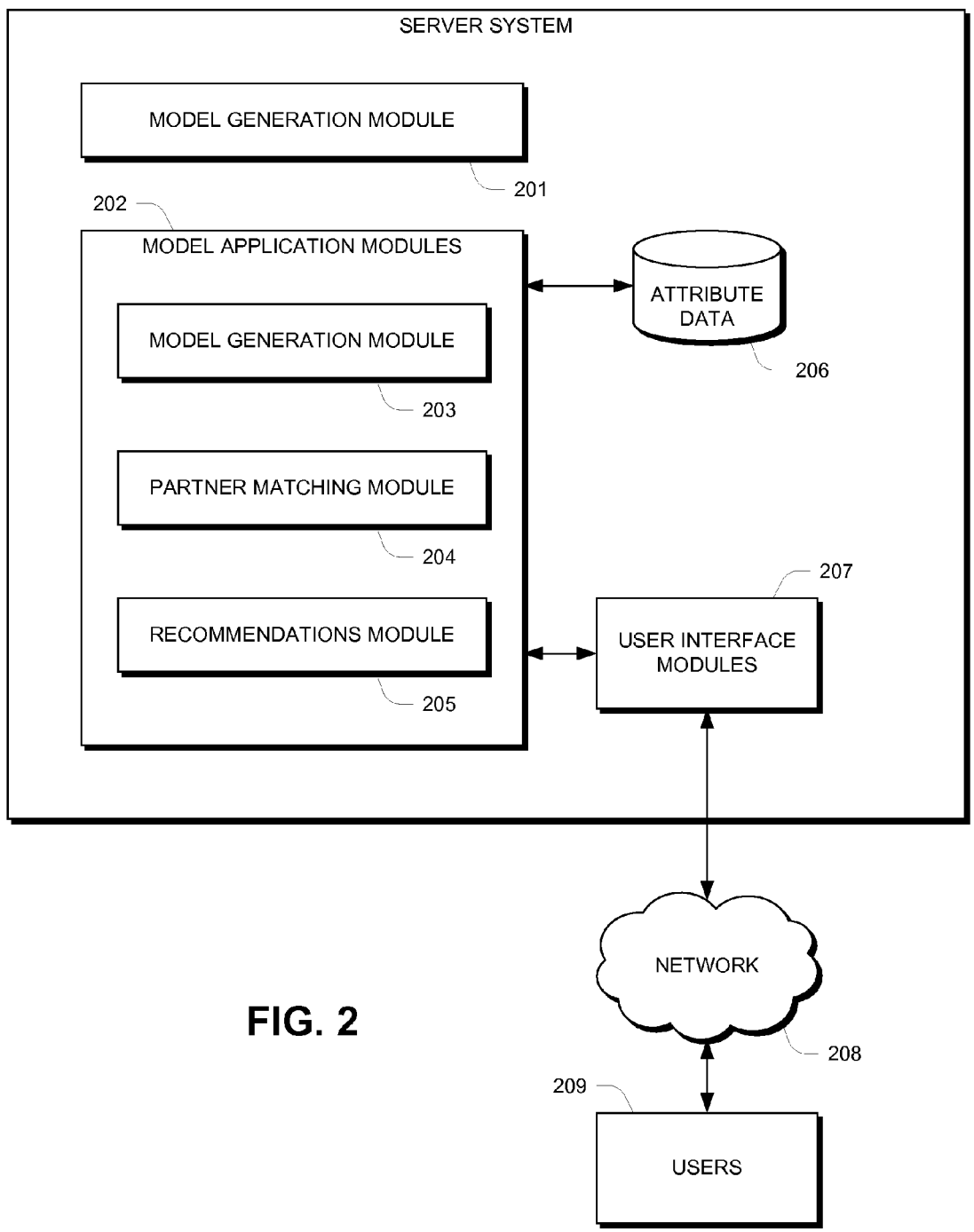
FIG. 2 is a block diagram of a computing system for modeling and matching partners, as used in an embodiment.

FIG. 2 is a block diagram of a computing system for modeling and matching partners, as used in an embodiment. In various embodiments, additional blocks may be included, some blocks may be removed, and/or blocks may be connected or arranged differently from what is shown.

Server 101 may include one or more modules which may be implemented as software or hardware. For example, server 101 may include model generation module 201. The model generation module may be configured to perform data analyses and generate one or more statistical or other models to be used by server 101. Model generation module 201 may generate models based on data collected at server 101 or elsewhere. In an embodiment, model generation module 201 may be configured to periodically update models to reflect further updated information, as gathered by server 101 or by another system. In an embodiment, model generation module 201 may be implemented using a mathematical and/or statistical programming system, such as SAS, S, R, Stata, Mathematica, and the like.

In an embodiment, model generation module 201 is configured to store information about generated modules on computer-readable storage within server 101 and/or at an external location. In an embodiment, model generation module 201 is located on a computing system different from server 101, and model information is transferred to server 101 via a communication link or the like. In an embodiment, rather than precalculating and storing models generated by model generation module 201, models are generated in real time, such as upon an appropriate user request.

Server 101 may further include model application modules 202. Such modules may be configured to use models generated by model generation module 201 in order to calculate information and/or user interfaces based on user inputs. In an embodiment, server 101 may include three model application modules, namely an ideal partner model 203, a partner matching module 204 and a recommendations module 205. In alternate embodiments, a subset of these modules may be included and/or additional modules may be included.

Ideal partner module 203 may be configured to determine the characteristics of an ideal partner for a particular individual based on that individual's attributes. Partner matching module 204 may be configured to match one or more individuals to one or more partners based on comparisons of outputs generated by various models used by the system. Recommendations module 205 may be configured to provide recommendations for behavioral, lifestyle and/or other aspects of an individual based on the user's desire for compatibility with partners or various desired attributes. Processes and operations performed by these and other modules are described in detail in this specification.

Attribute data 206 may include information about various attributes of individuals on the system. The attributes may be obtained via user input and/or analysis, such as surveys filled out by individuals on one or more web pages provided by server 101. The model application modules 202 may draw from attribute data 206 in making calculations about particular individuals and/or partners. Attribute data 206 may further include information about attributes of individuals not on the system. For example, attribute data 206 may include attributes of archetypal personalities, celebrities, historical figures, fictional characters, and/or the like.

User interface modules 207 may include one or more modules configured to generate user interfaces, such as web pages, desktop applications, mobile interfaces, voice interfaces, and the like. The user interface modules 207 may invoke the model application modules 202 in order to make calculations to be presented to individuals. The user interface modules 207 may then present data via network 208 to individuals 209. The user interface module 207 may further receive input from individuals 209 so that the input may be provided to the appropriate model application modules 202 and/or stored in attribute data 206.

Figure 3:
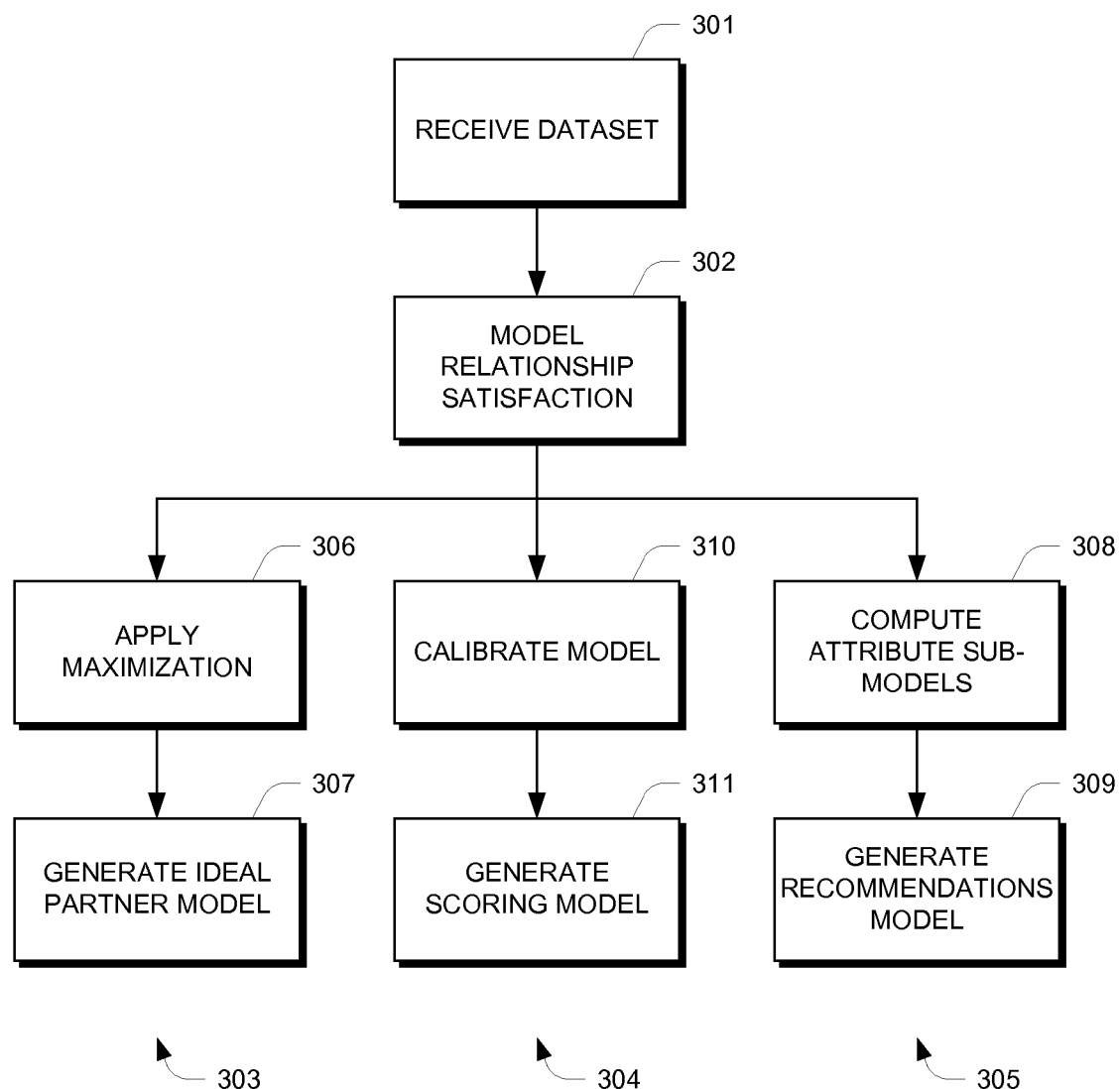
FIG. 3 is a process of generating models, as used in an embodiment.

FIG. 3 is a process of generating models, as used in an embodiment. The process may be performed, for example, by model generation module 201 of FIG. 2 and/or by another system. In various embodiments, additional blocks may be included, some blocks may be removed, and/or blocks may be connected or arranged differently from what is shown.

At block 301, the system receives a data set of attributes and/or relationship status information. The data set may be stored locally on the system and/or accessed from an external system. The data set may further be formatted using a variety of data formats, such as tab-delimited data, CSV files, Microsoft Excel files, relational database tables, statistical system data files, and/or the like. In an embodiment, the data set includes one or more records, with each record having a set of values for attributes and one or more values indicating a relationship status. The attributes may be used as independent variables and/or explanatory variables, and the relationship status may be used as a dependent variable and/or response variables.

At block 302, the system models the relationship status based on the attributes and/or interactions between the attributes. The model may be any appropriate statistical and/or nonstatistical model, such as a linear regression model, a multiple regression model, a probit regression model, a logit regression model, a decision tree, a neural network, or the like. In an embodiment, multiple models may be generated for different types of entities. For example, where the system is being used to match female and male partners, separate models for females and males may be generated. Further models may be used for different types of individuals based on characteristics such as location, age, appearance, family history, finances, and the like, thus enabling more accurate modeling and matching for particular demographics and/or groups.

In an embodiment, the modeling is performed based on interaction terms in addition to the attributes. Interaction terms may be used to identify synergistic and/or antagonistic relationships among attributes and/or nonlinear correlations of individual attributes. In an embodiment, two types of interactions may be used: quadratic interactions, calculated by squaring values for an attribute; and product interactions, calculated by multiplying the values of two attributes. In various embodiments, additional forms of interaction terms may be used.

Specific interaction terms that may be included, in various embodiments, include:

an interaction term for males' and females' levels of openness in relation to male relationship satisfaction.

an interaction term for males' and females' levels of conscientiousness in relation to male relationship satisfaction.

an interaction term for males' agreeableness and females' conscientiousness, in relation to female relationship satisfaction.

an interaction term for males' neuroticism and extroversion in relation to male relationship satisfaction.

an interaction term for males' neuroticism and agreeableness in relation to female relationship satisfaction.

an interaction term for males' agreeableness and conscientiousness in relation to female relationship satisfaction.

an interaction term for females' openness and agreeableness in relationship to male relationship satisfaction.

In various embodiments, additional interaction terms may be included and/or any subset of these interaction terms may be included. In an embodiment, the interaction terms to be included may be determined based on a statistical analysis of the data set received at block 301.

In an embodiment, the model of block 302 has the form:

$$S = f(i_1, i_2 \ldots i_n, p_1, p_2 \ldots p_n)$$

where S is a relationship satisfaction index for an individual, $i_1 \ldots i_n$ are attributes of the individual, $p_1 \ldots p_n$ are attributes of the partner. In an embodiment where the model is based on a linear and/or multiple regression, the model may have the form:

$$S = \sum_{z=1}^{n} a_z i_z + \sum_{z=1}^{n} b_z p_z + \sum_{y=1}^{n}\sum_{z=1}^{n} c_{yz} i_y i_z + \sum_{y=1}^{n}\sum_{z=1}^{n} d_{yz} p_y p_z + \sum_{y=1}^{n}\sum_{z=1}^{n} e_{yz} i_y p_z$$

where $a_1 \ldots a_n$ are coefficients for the individual, $b_1 \ldots b_n$ are coefficients for the partner, and $c_{11} \ldots c_{nn}$, $d_{11} \ldots d_{nn}$, and $e_{11} \ldots e_{nn}$ are coefficients for interaction terms.

In various embodiments, the model generated at block 302 may be used to generate one or more submodels. For example, subprocess 303 generates an ideal match model, subprocess 304 generates a matching model, and sub process 305 generates a recommendations model. These models may be used by model application modules 202 of FIG. 2. In an embodiment, a single model generated at block 302 is used for subprocesses 303-305. Alternately, separate models may be used for one or more of the subprocesses.

For the ideal match subprocess, at block 306, a maximization function may be applied to attributes of the model. The maximization function may be configured to optimize a subset of attributes of the model. For example, the maximization function may optimize the model with respect to attributes of a partner, given certain attributes for a particular individual. The result of the application of the maximization function at block 306 may be an ideal partner model generated at block 307. Such a model may be configured to retrieve a set of attributes for an individual as inputs, and produce a set of attributes for a hypothetical partner so that the partner and individual achieve maximum satisfaction.

In an embodiment, the maximization function is applied in advance to the model, so that the ideal partner model generated at block 307 may be applied to various attributes of individuals. In an alternate embodiment, the maximization function is applied after receiving the attributes for a particular individual. In such an embodiment, the maximization function may be applied in real time, for example, upon a request from the individual or other appropriate entity.

The maximization function may be any one or more of the known multidimensional optimization algorithms, such as hill-climbing, simulated annealing, random sampling, genetic algorithms, and so on. It is well known that maximization and optimization are difficult computational problems, so absolute maximization or optimization may not be required in various embodiments. For example, in an embodiment, an identified local maximum may be generated by the ideal partner model. In an embodiment, the model may instead identify attributes for a partner such that the resulting relationship satisfaction exceeds a threshold. In an embodiment, the possible values for attributes generated by the ideal partner model are capped at appropriate limits to ensure that the model does not suggest an ideal partner with unrealistic attributes. Similarly, although the identified attributes are described herein as identifying an "ideal" partner, it is not necessary that the partner be "ideal," but in various embodiments the attributes may identify a preferable or sufficiently compatible partner.

In the matching subprocess 304, at block 310, the model generated at block 302 may be calibrated to produce an appropriately scaled score. In an embodiment, the model is calibrated based on the mean and standard deviation of the dependent variables of the data set received at block 301. The calibration may be used so that the model produces a score and/or percentile value. In an embodiment, where the model generated at block 302 already produces appropriate values, no calibration may be required at block 310. The result of the calibration at block 310 is a scoring model generated at block 311, In the recommendations subprocess 305, recommendations submodels may be generated at block 308. In an embodiment, the recommendations submodels may include a separate model for each attribute provided by an individual. The submodel would use as input attribute values for an individual and that individual's desired partner. In an embodiment, recommendations may be generated based on the individual's attributes alone or in combination with other data. In an embodiment, recommendations may be generated based on the partner's attributes alone or in combination with other data. In an embodiment, further inputs, such as inputs indicative of the individual's desires, may be used as inputs to the submodels.

In an embodiment, each submodel is computed as a partial derivative of the model generated at block 302 with respect to each of the individual's attributes. The resulting submodels may be used to generate a recommendations model at block 309.

FIG. 4 is a sample user interface of a survey for assessing personality attributes, as used in an embodiment. Interface 401 includes a self-survey of personality attributes. The survey may ask one or more questions of an individual. The questions may be directed to aspects of the individual filling out the survey, attributes of that individual's current and/or desired partner, and/or other attributes. The attributes may be the same as the attributes used in the various models, as described throughout the specification, and/or other attributes.

Interface 402 may be displayed after the survey responses from interface 401 are submitted to the system. Interface 402 may display one or more attribute values that may be calculated using the inputs provided from interface 401. In alternate embodiments, the values shown in interface 402 may be internally stored and not displayed to the individual.

Figure 5:
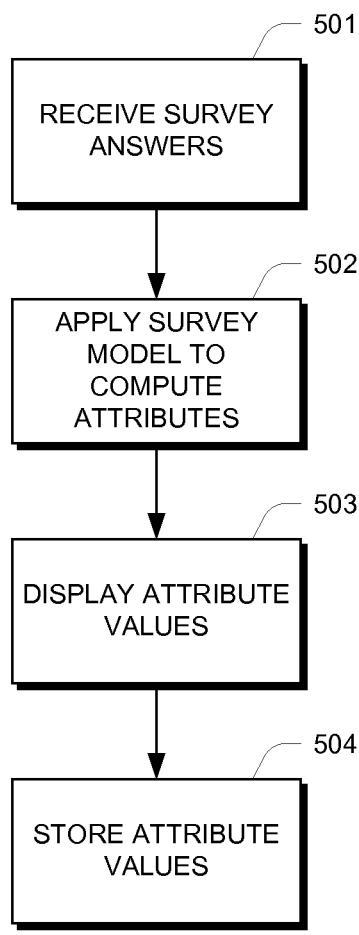
FIG. 5 is a process of determining attribute values for an individual, as used in an embodiment.

FIG. 5 is a process of determining attribute values for an individual, as used in an embodiment. The process may be performed by server 101 of FIG. 1 and/or by another system. In various embodiments, additional blocks may be included, some blocks may be removed, and/or blocks may be connected or arranged differently from what is shown.

At block 501, the system receives survey answers. The survey answers may be received, for example, from an interface, such as interface 401 of FIG. 4. At block 502, a survey model may be applied to compute attributes based on the survey answers received at block 501.

In an embodiment, the questions presented correspond to a standard psychological questionnaire, such as the Mini-Modular Markers (3M40), the Minnesota Multiphasic Personality Inventory (MMPI), and the like. In an embodiment, the 3M40 inventory is used, as it corresponds to the five attributes identified previously.

At block 503, the attributes computed at block 502 may be displayed to the individual who provided the survey answers at block 501. In an alternate embodiment, the values need not be displayed. At block 504, the values are stored in the system and/or at another location. In an alternate embodiment, the values need not be stored and may instead be entered by the individual as necessary, thereby protecting the privacy of the individual.

Figure 6:
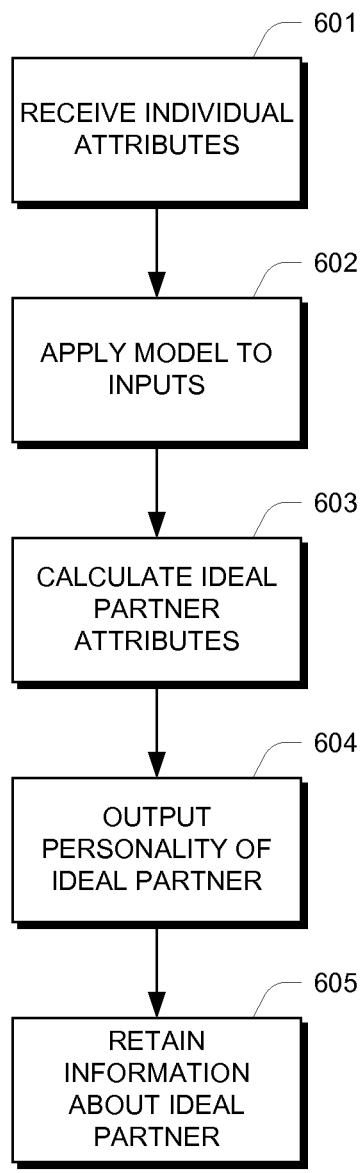
FIG. 6 is a flowchart of a process of determining an ideal partner for an individual.

FIG. 6 is a flowchart of a process of determining an ideal partner for an individual. The process may be performed, for example, by ideal partner module 203 of FIG. 2. In various embodiments, additional blocks may be included, some blocks may be removed, and/or blocks may be connected or arranged differently from what is shown.

At block 601, user input is received from the individual. The input may include one or more attributes relating to the individual. Additionally or alternatively, the attributes may be retrieved from storage within the system. At block 602, the appropriate model or algorithm is used to compute attributes for an ideal partner at block 603.

Based on this calculation, various outputs may be provided. For example, at block 604, the system outputs information relating to the personality of the ideal partner determined at block 603. The personality may be indicated by the values of the attributes themselves, and/or through related information, such as textual descriptions, graphics, charts, information about individuals similar to the ideal profile, and the like. Alternately, at block 605, feedback may not be provided to the user about the attributes of the computed ideal partner. Instead, the computed attributes may be used for further computations for the individual.

Figure 7:
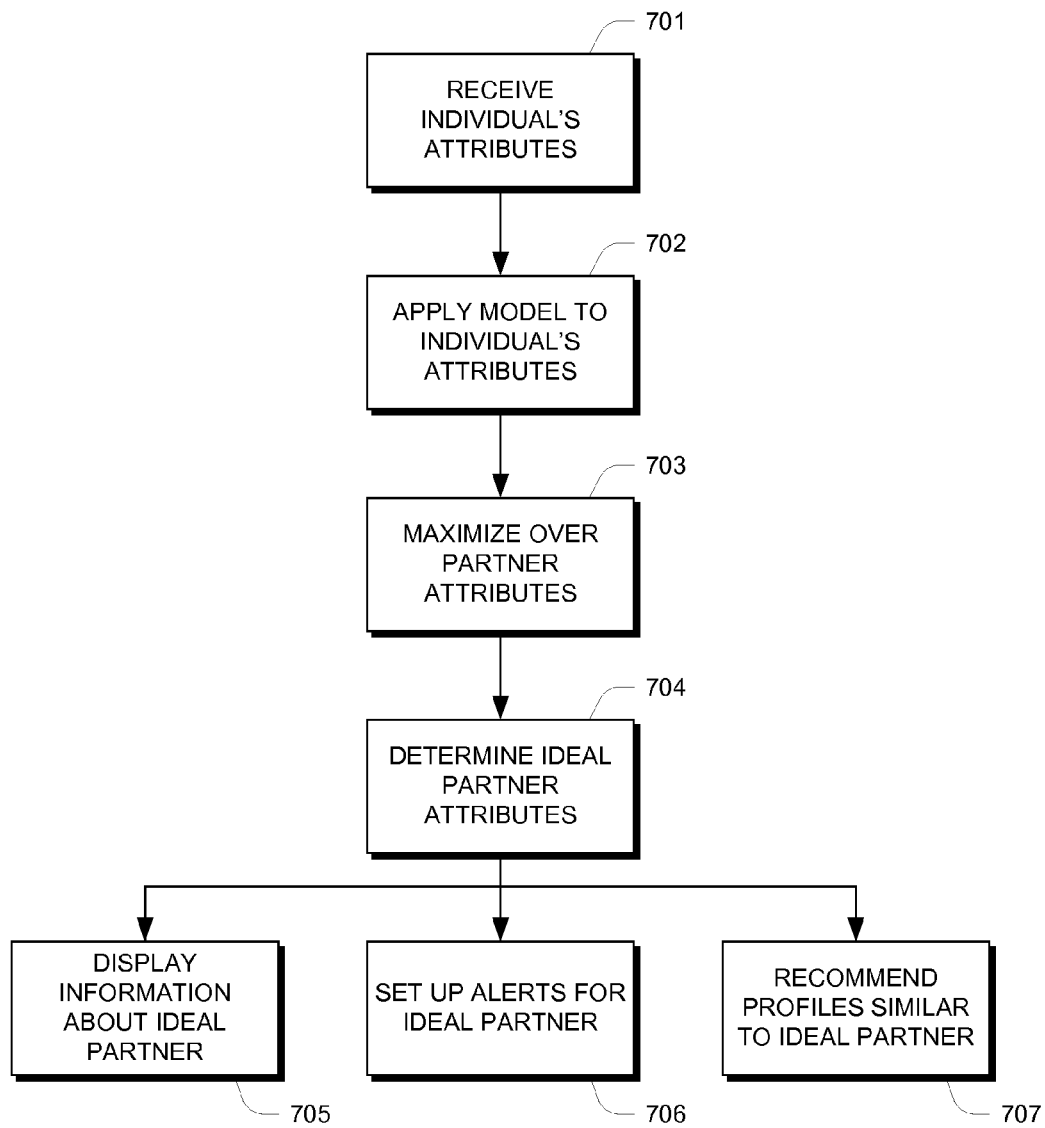
FIG. 7 is a flowchart of a process of determining an ideal partner, as used in an embodiment.

FIG. 7 is a flowchart of a process of determining an ideal partner, as used in an embodiment. The process may be an expansion and/or alternate process to that shown in FIG. 6. The process may be performed, for example, by ideal partner module 203 of FIG. 2. In various embodiments, additional blocks may be included, some blocks may be removed, and/or blocks may be connected or arranged differently from what is shown.

At block 701, attributes relating to an individual are received. At block 702, a model may be applied to the attributes received at block 701. In an embodiment, the model takes as inputs attributes about an individual and a partner in order to compute a predicted relationship satisfaction score. Thus, in an embodiment, the application of the individual's attributes at block 702 does not provide a full set of inputs to the model. In other words, the model may still include one or more free variables, namely the attributes of a potential partner for the individual.

At block 703, the model from block 702 is maximized over the partner attributes. Thus, the maximization may be computed over the free variables, as described with respect to block 702. The maximization process may be one or more of the known maximization or optimization algorithms, as described previously. Also as described previously, the maximization process at block 703 need not calculate an absolute maximum, but rather may compute a local maximum and/or values that meet a certain threshold of relationship satisfaction.

Based on the maximization or calculation process of block 703, the ideal partner attributes are determined at block 704. In an embodiment, the ideal partner attributes are values for attributes of a potential partner for the individual. In an embodiment, the ideal partner attributes are ranges of values for those attributes. For example, at block 703, the model may be used to compute ranges of attribute values so that the model relationship satisfaction exceeds a threshold value provided by the individual or other entity. In another embodiment, at block 704, two or more sets of attributes may be computed. This may occur, for example, where the model of block 702 has multiple local maxima, such as in a bimodal distribution.

The ideal partner attributes may then be used for a variety of outputs to the individual and/or other entities. Any one or more of these outputs may be used and/or other outputs may be generated. Additionally, the outputs may be used as inputs to other components of the system and/or other systems. One such use is described with respect to FIG. 16.

In an embodiment, at block 705, information about the ideal partner may be displayed. In an embodiment, the information is displayed to the individual whose attributes were received at block 701. In alternate embodiments, the information may be displayed to another entity, such as a third-party evaluator. In some embodiments, the numeric attributes are not displayed, but rather are stored and used as inputs to another component. Maintaining the confidentiality of these numbers may further objectives such as privacy, ethical considerations, business technology protections, and so on.

In an embodiment, at block 706, the system sets up alerts to search for individuals based on the ideal partner attributes determined at block 704. For example, the system may be configured to analyze new users who sign up with the system to determine whether those users fall within a certain range of the ideal partner attributes. Thus, the individual whose attributes were received at block 701 may receive a notification at the time that a user sufficiently close to that individual's ideal partner signs up. Additionally or alternatively, the system may periodically monitor for individuals satisfying the requisite conditions. The time period for monitoring may be customizable by the individual and/or other entity.

In an embodiment, at block 707, the system may recommend one or more profiles similar to the ideal partner determined at block 704. The recommended profiles may be drawn from existing profiles of other users on the system. Additionally or alternatively, the recommended profiles may be fictitious entities and/or celebrities or other individuals not signed up for the system. Such recommendations may be useful, for example, for providing archetypal examples of potential partners for the individual. These examples may be more useful than displaying raw attributes about the individual's ideal partner.

Figure 8:
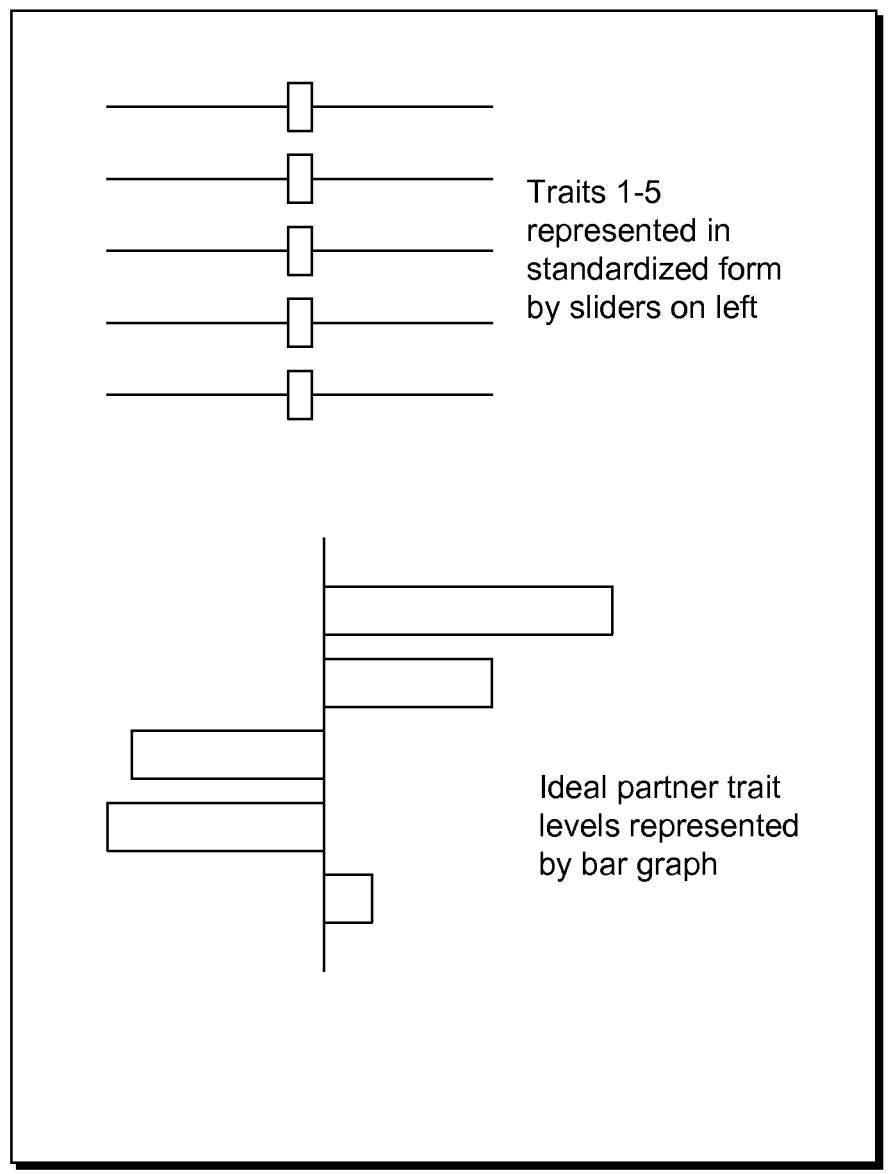
FIG. 8 is a sample user interface for viewing and adjusting parameters for an ideal partner calculation, as used in an embodiment.

FIG. 8 is a sample user interface for viewing and adjusting parameters for an ideal partner calculation, as used in an embodiment. As shown in FIG. 8, the server can output the ideal partner feedback as a bar graph of the hypothetical ideal partner's personality index. However, other graphical representations or raw numbers can also be used. This feedback can also be provided as a narrative description of the ideal partner, either alone or in combination with the bar graph or other graphical representation of the personality index. According to at least one embodiment, and as shown in FIG. 8, the user's personality index can be displayed on slider bars. In this example, the five slider bars represent, from the top, openness, conscientiousness, extraversion, agreeableness, and neuroticism. The user can adjust the sliders, which causes the server to dynamically change the corresponding ideal partner shown below the slider. The five bars in the ideal partner portion again represent openness, conscientiousness, extraversion, agreeableness, and neuroticism. This can allow the partner to see how changes in the user's personality can affect his or her ideal partner match.

Alternatively to the embodiment of FIG. 8, the bar graph may not be displayed, but rather replaced with other representations of information relating to the ideal partner calculation. The particular values of attributes calculated here, or in any of the various embodiments described herein, may be maintained confidential by the system to further the various objectives described above.

A particular combination of the attribute-specific slider bars shown in FIG. 8 corresponds with a particular combination of attribute-specific bars in the "ideal partner profile." As the slider bars change, the ideal partner bars may change in accordance with an underlying model. This is because each ideal partner trait may be a determined as a function of all five trait settings of the current user. The relationships that specify how the ideal partner trait values are calculated are typically based on survey data collected from many hundreds or thousands of users. Other interface elements may also be used in place of or in addition to sliders, such as text input boxes, drop-down boxes, dials, spinners, and so on.

Although not shown in FIG. 8, the system's user interface may also include a button or other control for enabling the current user to initiate a search for partners whose respective personality indexes are close to that of the hypothetical ideal partner. To execute such a search, the server may compare the ideal partner profile to the profiles of existing users/subscribers, with different amounts of weight optionally given to different traits. In executing the search, the server may also apply other partner criteria or filters specified by the current user, such as age range, gender, geographic region, and so on. The server may then output to the current user a ranked list of individuals whose profiles closely match the ideal partner profile, optionally together with a graphical or other indication of how the profile of each such individual differs from that of the ideal profile. The system may also provide an appropriate messaging function for enabling the current user to contact one or more of the recommended individuals.

Figure 9:
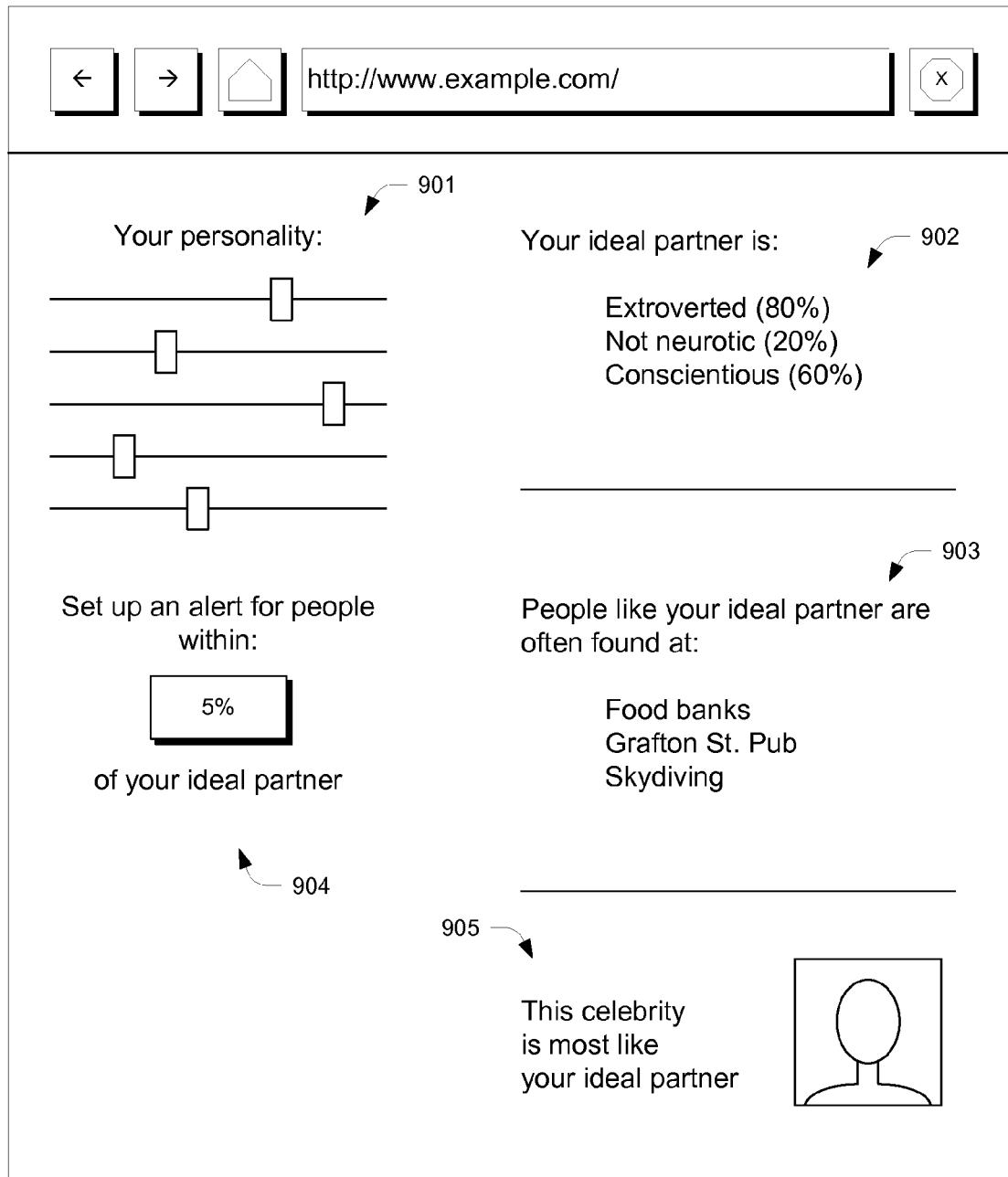
FIG. 9 is a sample user interface displaying information about a calculated ideal partner, as used in an embodiment.

FIG. 9 is a sample user interface displaying information about a calculated ideal partner, as used in an embodiment. The user interface may be displayed, for example, at the conclusion of the process described with respect to FIG. 7.

The interface may include an indication of the personality attributes of the individual requesting ideal partner information. These attributes may be displayed, for example, at interface element 901. The attribute values may be displayed as movable sliders, thus allowing the individual to experiment with different hypothetical values of those attributes. In an embodiment, when the individual updates the values of the sliders, other information on the user interface may be updated automatically and/or in real time. Such real-time updating may be enabled, for example, through an embedded script and/or through one or more asynchronous HTTP and/or other network requests. Other interface elements may also be used in place of or in addition to sliders, such as text input boxes, drop-down boxes, dials, spinners, and so on.

Interface element 902 displays information about the ideal partner, as computed by the system. In an embodiment, the description may include text, graphics, charts, and/or other descriptions. Further information about the ideal partner may also be displayed. For example, interface element 903 displays recommendations and/or information about people like the computed ideal partner. For example, the interface may display places that people like the calculated ideal partner may tend to frequent. Interface element 904 may display a celebrity and/or other individual that is most like the computed ideal partner. This may be computed, for example, at block 707 of FIG. 7.

Interface element 905 may enable the individual to set up an alert for people that come within a certain threshold of the calculated ideal partner. The threshold may be customizable by the user. In various embodiments, the user may configure the frequency of monitoring for the ideal partner and/or the methods of alerts, such as email, text messages, in-website messages, messages to the identified potential partner, and the like.

Figure 10:
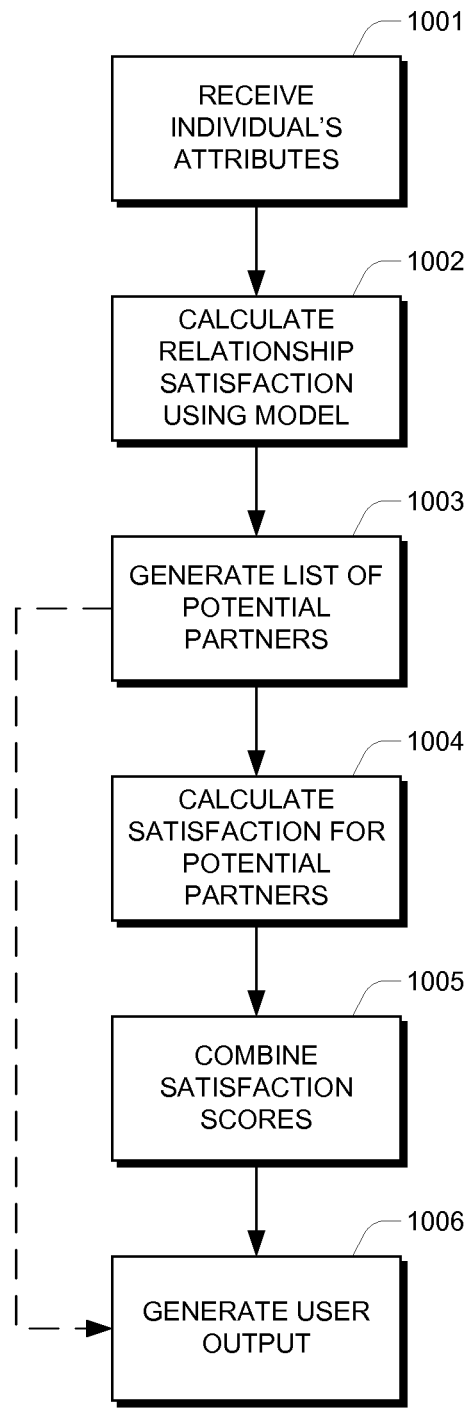
FIG. 10 is a flowchart of a process of matching individuals, as used in an embodiment.

FIG. 10 is a flowchart of a process of matching individuals, as used in an embodiment. The process may be performed, for example, by partner matching module 204 of FIG. 2. In various embodiments, additional blocks may be included, some blocks may be removed, and/or blocks may be connected or arranged differently from what is shown.

At block 1001, user input is received relating to attributes of an individual. Additionally or alternatively, the attributes may be retrieved from storage within the system. At block 1002, an appropriate model is applied to the attributes from block 1001 and information about potential partners is stored on the system. The results of the calculation at block 1002 are used to generate a list of matches at block 1003. In an embodiment, the matches generated at block 1003 are limited based on geographic locality. In an embodiment, other factors may be used to limit the list at block 1003, such as age, profession, appearance, personal interests, and so on.

Optionally, a second level of comparison may be performed. At block 1004, for each of the potential partners identified at block 1003, a second computation is performed using a model to determine the relationship satisfaction for the potential partner in view of the individual whose attributes were received at block 1001. At block 1005, the list of matches is adjusted based on the application of the model at block 1004. This may account for discrepancies of satisfaction between the two parties. For example, an individual may be predicted by a model to be highly satisfied with a particular potential partner, but that potential partner may be predicted to be highly unsatisfied with the individual. Accordingly, such a match may be undesirable.

At block 1006, feedback is provided to the individual about the potential matches. The feedback may include one or more user interfaces identifying the potential partners.

Figure 11:
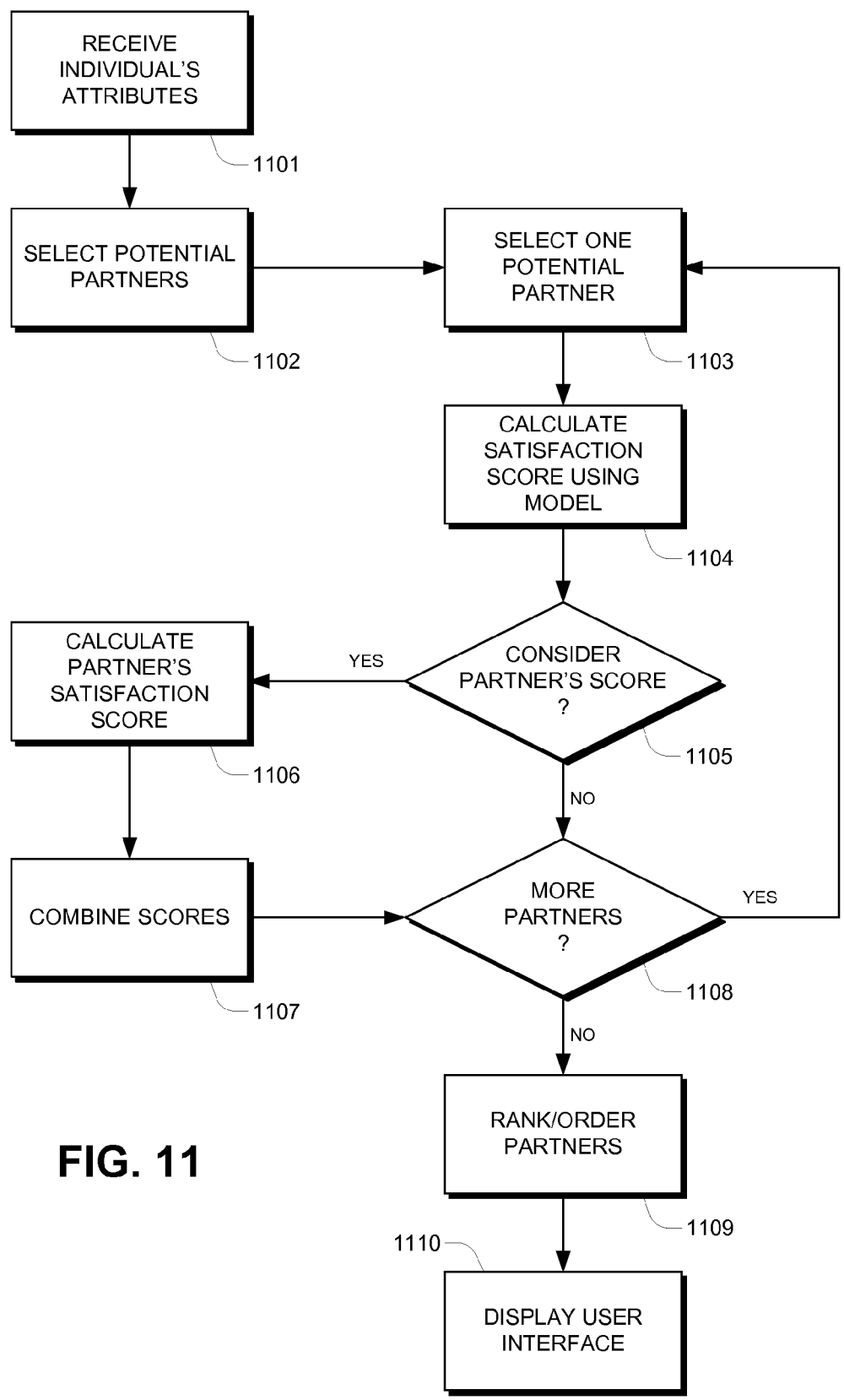
FIG. 11 is a flowchart of a process of matching partners, as used in an embodiment.

FIG. 11 is a flowchart of a process of matching partners, as used in an embodiment. The process may be used as an expansion of and/or alternative to the process shown with respect to FIG. 10. The process may be performed, for example, by partner matching module 204 of FIG. 2. In various embodiments, additional blocks may be included, some blocks may be removed, and/or blocks may be connected or arranged differently from what is shown.

At block 1101, attributes relating to an individual may be received and/or retrieved from storage. At block 1102, potential partners are selected from the system. The potential partners may include all of the users on the system. Alternatively, a subset of those users may be selected as potential partners, thereby reducing the computational load on the system. The potential partners may be selected using one or more factors. For example, they may be selected using an ideal partner profile computed by a process such as that shown in FIGS. 6 and 7. Potential partners may further be selected based on information such as geographic location, age, appearance, personal information, and the like. Potential partners may additionally or alternatively be selected by the individual whose attributes were received at block 1101. For example, the individual may select several potential partners that the individual is interested in, so that the individual may discover which of those potential partners is the most compatible. The individual may select only a single potential partner in an effort to determine the degree of potential compatibility between the individual and that single potential partner, thereby improving on the traditional methodology of removing petals from a flower.

At block 1103, one partner is selected from the list of potential partners selected at block 1102. At block 1104, an appropriate model is applied to compute a relationship satisfaction score between the individual and the selected potential partner. At block 1105, the system may optionally consider a relationship satisfaction score for the partner, as explained previously with respect to blocks 1004 and 1005 of FIG. 10. If the partner score is to be considered, then at block 1106, an appropriate model is applied to calculate a relationship satisfaction score for the partner. At block 1107, the two calculated scores may be combined, for example, by adding them. In various embodiments, the scores may be given different weights. For example, if the individual values, the potential partner's satisfaction more highly, then the score at block 1106 may be weighted more heavily than the score calculated at block 1104 when combining the scores at block 1107.

At block 1108, the list of potential partners is considered and if there are further potential partners to consider, then the process returns to block 1103. Otherwise, the selected partners may be rank ordered by the calculated scores at block 1109. The rank order list and/or the scores may be used to display one or more user interfaces at block 1110.

Figure 12:
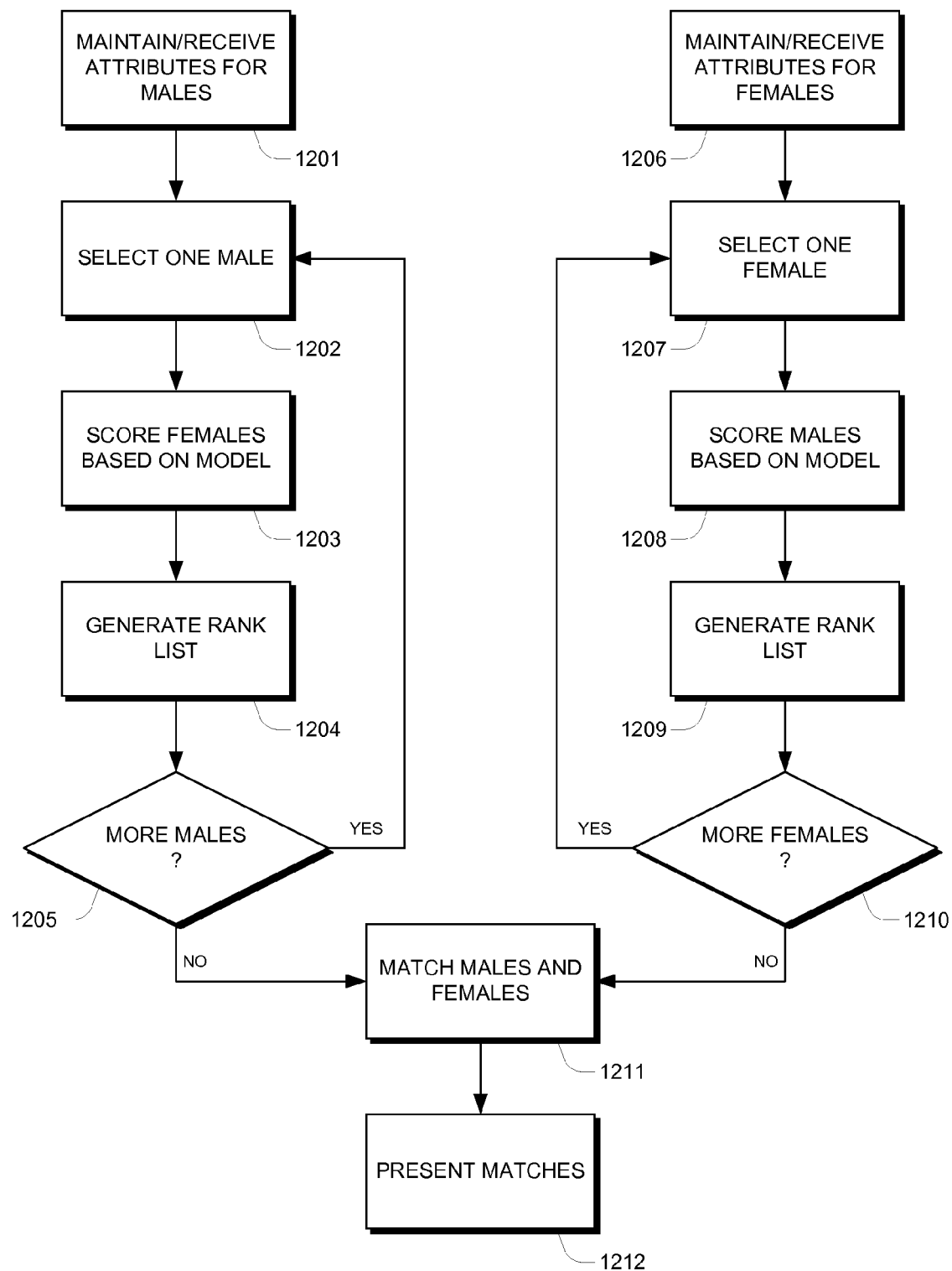
FIG. 12 is a flowchart of a process of matching a set of individuals, as used in an embodiment.

FIG. 12 is a flowchart of a process of matching a set of individuals, as used in an embodiment. The process may be performed by partner matching module 204 of FIG. 2. In various embodiments, additional blocks may be included, some blocks may be removed, and/or blocks may be connected or arranged differently from what is shown.

The process of FIG. 12 may be used to match a community of individuals. This is distinguished from the process of FIGS. 10 and 11, which matched a set of partners to a single individual. For example, the process of FIG. 12 may be used to match a class of students for a school dance. In a context outside of personal relationships, the process of FIG. 12 may be used, for example, to match applicants to schools and/or job positions. Although the process of FIG. 12 is described with respect to males and females, it will be understood that it may be applied to matching of different types of entities.

At block 1201, attributes for a set of male individuals are received and/or maintained by the system. At block 1202, one of those males is selected. At block 1203, the system applies a model to the selected males' attributes, and the attributes of the female individuals on the system, thereby computing relationship status scores for each of the females. In various embodiments, as described with respect to FIGS. 10 and 11, the score may consider the male's satisfaction, the female's satisfaction, and/or a combination. Based on the scores computed at block 1203, a rank list may be generated at block 1204. The rank list may thus indicate the predicted preferences among the females for the selected male. At block 1205, the process returns to block 1202 to generate rank lists for the remaining males within the group.

The results of blocks 1201-1205 is a rank list, for each of the males, of all of the females within the group. A corresponding process is then performed with respect to the females, at blocks 1206-1210.

At block 1211, the males and females are matched, based on the rank lists generated at blocks 1204 and 1209. The matching process may be analyzed as a version of the stable marriage problem, so that the matching may be performed using the Gale-Shapely algorithm, or other appropriate algorithm. In an embodiment, the computed scores may be considered in addition to the rank lists, so that the degree of satisfaction may be incorporated into the matching process.

At block 1212, the computed matches are presented. The matches may be individually sent to the appropriate individuals, and/or displayed on a listing interface.

Figure 13:
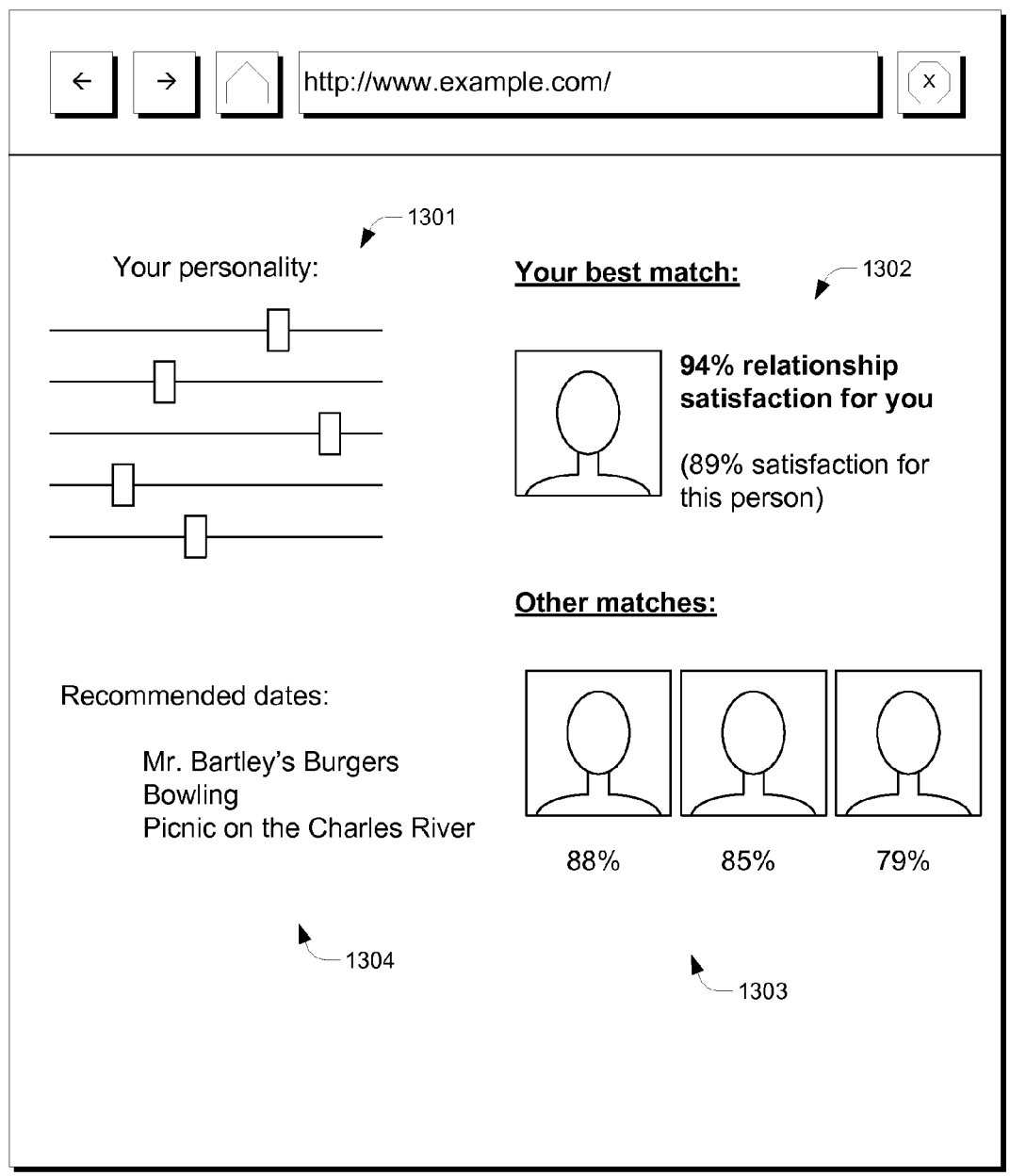
FIG. 13 is a sample user interface displaying partner matching results, as used in an embodiment.

FIG. 13 is a sample user interface displaying partner matching results, as used in an embodiment. The user interface may be displayed, for example, at block 1006 of FIG. 10, at block 1110 of FIG. 11, and/or at block 1212 of FIG. 12. In various embodiments, additional blocks may be included, some blocks may be removed, and/or blocks may be connected or arranged differently from what is shown.

The interface may include indications of the individuals' attributes at interface element 1301. The attributes may be adjustable, as described with respect to interface element 901 of FIG. 9.

Interface element 1302 may display the best match identified by the matching process. The listing may include profile information about the best match, such as the potential partner's photo, personal information, location, contact information, and the like. Interface element 1302 may further display one or more indications of predicted relationship satisfaction, as computed by the matching process. The indications may include an indication of the individual's predicted satisfaction with the recommended partner, and/or the recommended partner's predicted satisfaction with the individual.

At block 1303, other potential partners selected by the matching process may be displayed. Those partners may be selected and/or ordered based on the relationship satisfaction scores, as computed by the matching process.

Interface element 1304 may provide auxiliary information relating to the identified match. Such information may include, for example, a list of recommended dates with the selected potential partner, a list of common interests, a list of common friends, suggestions and recommendations for the individual, as described elsewhere in the specification, and the like.

Figure 14:
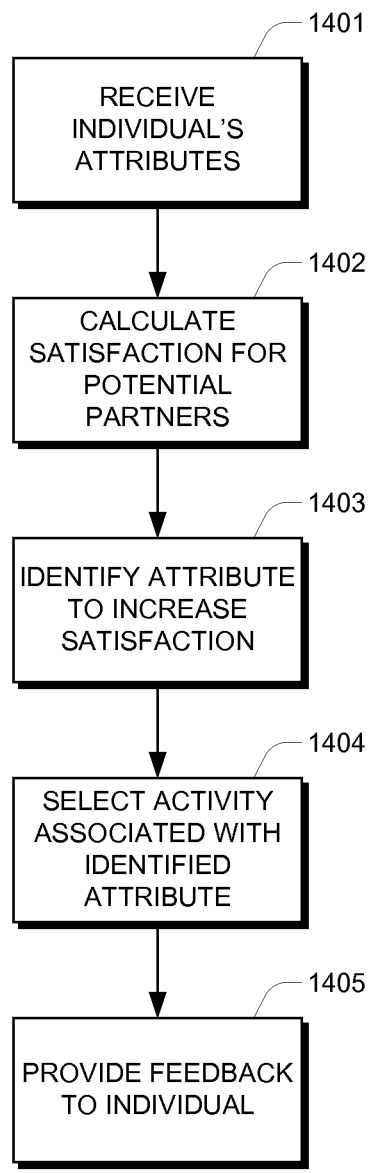
FIG. 14 is a flowchart of a process of generating recommendations for an individual, as used in an embodiment.

FIG. 14 is a flowchart of a process of generating recommendations for an individual, as used in an embodiment. The process may be performed, for example, by recommendations model 205 of FIG. 2. In various embodiments, additional blocks may be included, some blocks may be removed, and/or blocks may be connected or arranged differently from what is shown.

Recommendations are of great value to an individual seeking potential partners. The individual may wish to be more compatible with a certain type of potential partner and/or with a certain potential partner or partners. The individual may, alternatively, simply desire to be more compatible with more partners generally. Thus, by using a relationship satisfaction model to generate recommendations, the individual receiving the recommendations may be greatly advantaged.

At block 1401, user input is received indicating one or more attributes of an individual. The attributes may alternatively be prestored on the system so that they need not be requested. The system calculates a predicted relationship satisfaction score for a potential partner selected by the individual. The score may be calculated using an appropriate relationship satisfaction model.

At block 1403, the system identifies an attribute of the individual that may be changed to increase the predicted relationship satisfaction, as calculated by the model. The selection of the attribute may be performed using a variety of means. For example, an attribute-based submodel may be applied, such as those described with respect to blocks 308 and 309 of FIG. 3. The attribute may be selected based on computed partial derivatives of the model with respect to the user's current attributes. The attribute may additionally or alternatively be selected using a maximization computation, as described previously, and/or by simulating various changes to the individual's attributes. In an embodiment, rather than selecting a single attribute to change, multiple attributes may be identified at block 1403, possibly in conjunction with a ranking and/or degree to which each attribute should be changed.

At block 1404, an activity is selected based on the attribute identified at block 1403. In an embodiment, the activity is selected from a database correlating activities with particular personality traits or other attributes. The activities may be selected to modify or otherwise adjust the appropriate attributes of the individual. For example, where an increase to extroversion is suggested at block 1403, the suggested activity at block 1404 may be a large party. At block 1405, appropriate feedback is provided to the individual, such as through one or more user interfaces.

Figure 15:
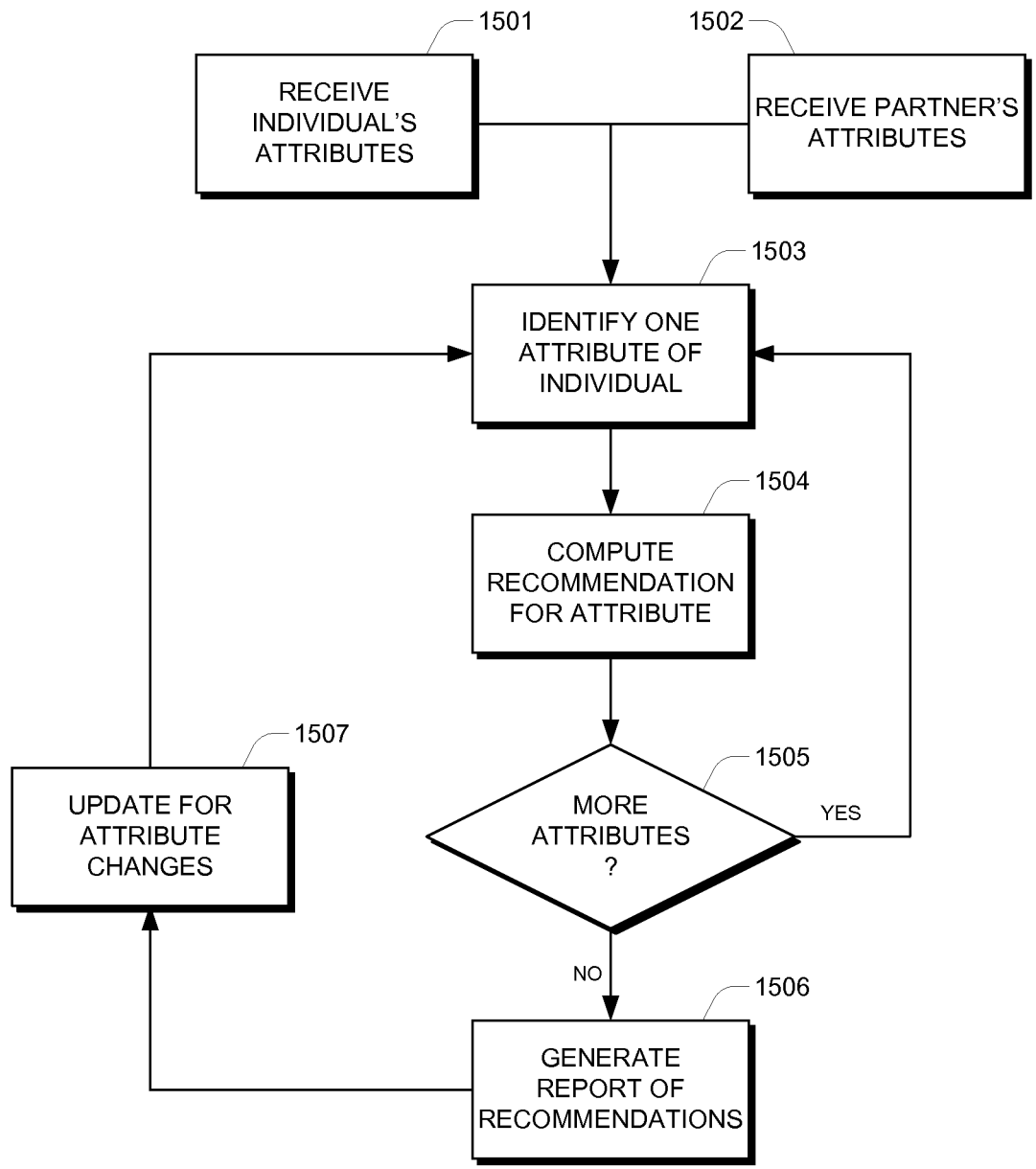
FIG. 15 is a flowchart of a process of making recommendation to an individual, as used in an embodiment.

FIG. 15 is a flowchart of a process of making recommendation to an individual, as used in an embodiment. The process may be performed, for example, by a recommendations module 205 of FIG. 2. The process may be used as on expansion of and/or alternative to the process shown with respect to FIG. 14. In various embodiments, additional blocks may be included, some blocks may be removed, and/or blocks may be connected or arranged differently from what is shown.

At block 1501, attributes relating to an individual may be received and/or retrieved from the system. At block 1502, attributes relating to a partner may be received and/or retrieved. The partner attributes may be provided by the same individual who provided the attributes at block 1501. Alternately, the partner attributes may be selected based on a desired potential partner selected by the individual or other entity. In an embodiment, the partner attributes may be based on a celebrity or a fictional character selected by the individual or other entity.

At block 1503, one of the attributes of the individual is selected. At block 1504, an appropriate model is used to compute a recommendation with regard that selected attribute, based on the individual's attributes received at block 1501 and the partner's attributes of block 1502. In an embodiment, the recommendation is a score indicating which direction and how much the individual should change the selected attribute in order to improve relationship satisfaction with the particular partner of block 1502. At block 1505, the process returns to block 1503 so that it may be repeated across the individual's attributes. In an alternate embodiment, all of the attributes may be considered simultaneously so that interactions between the recommendations for each of the attributes may also be considered.

At block 1506, a report of the recommendations may be generated based on the recommendations produced at block 1504. The report may include suggested changes to the individual's attributes, recommended activities for the individual, people that the individual should emulate to achieve the recommendations, a style and/or clothing advisor, and the like.

At block 1507, changes to the individual's attributes may be received. The changes may be provided, for example, by the individual in an effort to simulate having different personality attributes. Upon receiving such updates to those attributes, the process returns to block 1503 to repeat the determination of recommendations. In am embodiment, the updating may be performed in real time so that the individual may quickly view the affect of changes to the individual's personality attributes.

Recommendations may also be calculated using processes different from those described with respect to FIGS. 14 and 15.

Figure 16:
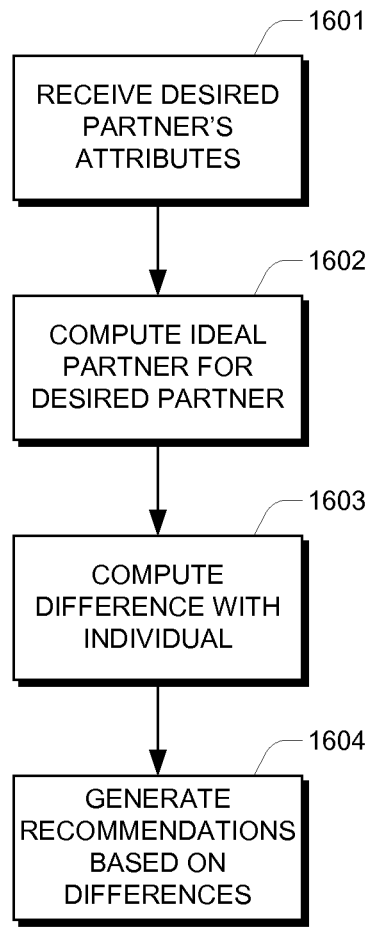
FIG. 16 is a flowchart of a process of making recommendations to an individual based on computed ideal partner attributes, as used in an embodiment.

FIG. 16 is a flowchart of a process of making recommendations to an individual based on computed ideal partner attributes, as used in an embodiment. According to this embodiment, recommendations for changes to an individual may be made, based on an ideal partner computed for a desired partner for the individual. In other words, if an individual A is interested in a potential partner B, the system can compute an ideal partner C for person B, and determine differences between person A and ideal partner C to generate recommendations. In various embodiments, additional blocks may be included, some blocks may be removed, and/or blocks may be connected or arranged differently from what is shown.

At block 1601, the system receives attributes for a desired partner of the individual. At block 1602, the system computes attributes for an ideal partner based on the received attributes from block 1601. The ideal partner attributes may be computed using a process such as those shown with regard to FIGS. 6 and 7. The attributes computed at block 1602 thus represent an ideal that the individual may wish to obtain in order to be desirable to the individual's desired partner.

At block 1603, the system computes a difference between the individual's attributes and the attributes of the ideal partner. At block 1604, recommendations may be generated based on the differences computed at block 1603, and those recommendations may then be reported to the individual or other appropriate entity.

Figure 17:
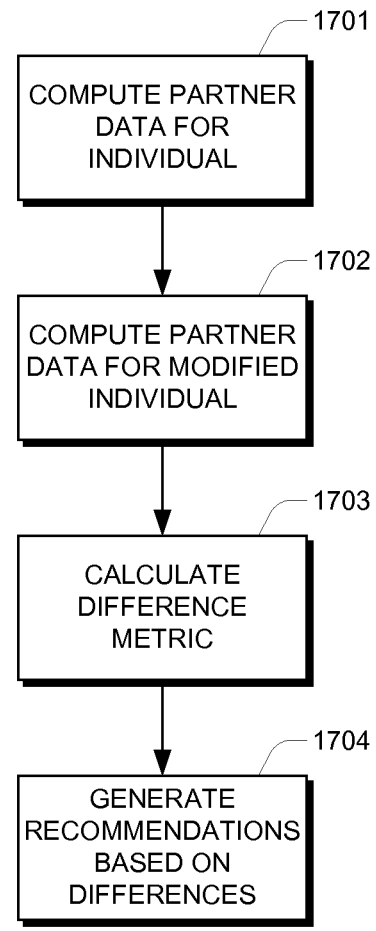
FIG. 17 is a flowchart of a process of making recommendations to an individual as to how that individual can increase the number of potential matches, as used in an embodiment.

FIG. 17 is a flowchart of a process of making recommendations to an individual as to how that individual can increase the number of potential matches, as used in an embodiment. For example, some individuals may find themselves to be incompatible with many other users on the system and simply desire to find out how they can increase their numbers of matches overall. In various embodiments, additional blocks may be included, some blocks may be removed, and/or blocks may be connected or arranged differently from what is shown.

At block 1701, the system computes information relating to potential partners for the individual. The information may be ideal partner attributes, a number of matches with potential partners, an average relationship satisfaction score, or the like. At block 1702, a similar computation is performed, except with respect to modified attributes for the individual.

At block 1703, a difference between the information computed at block 1702 and the information computed at block 1701 may be calculated. For example, where the computations at blocks 1701 and 1702 were ideal partner attributes, the difference at block 1703 may be a metric of the attainability of the computed ideal partners. Where the computations at blocks 1701 and 1702 are a number of matches, the difference at block 1703 may be a difference in the number of matches.

The computations at blocks 1702 and 1703 may then be repeated for various modifications to the individual's attributes. In alternate embodiments, rather than repeating the computations, the values of the modified attributes for the individual may be selected using a maximization process as described previously. At block 1704, recommendations based on the differences computed at block 1703 may then be generated and displayed on an appropriate user interface.

Figure 18:
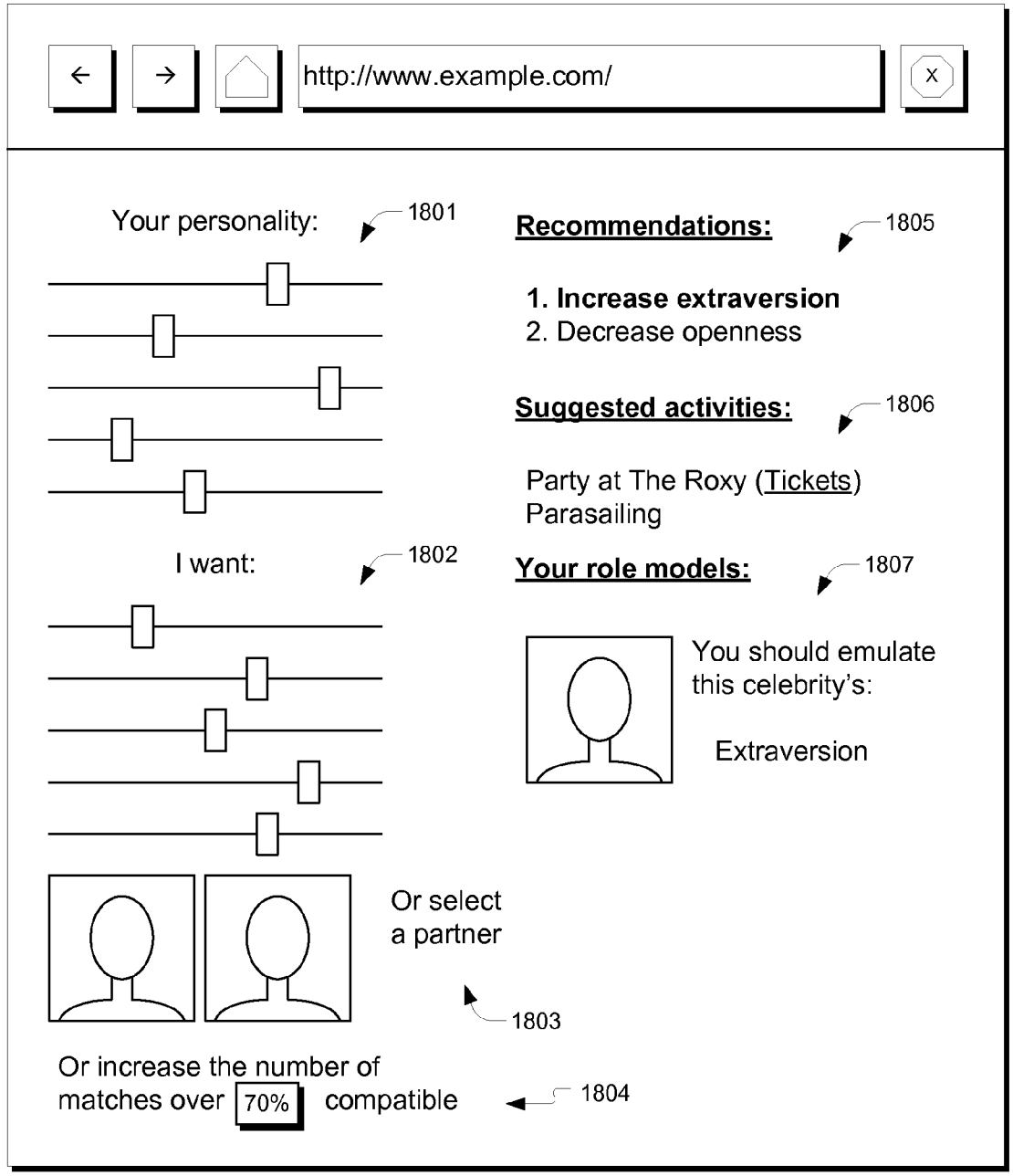
FIG. 18 is a sample user interface for reporting recommendations to an individual, as used in an embodiment.

FIG. 18 is a sample user interface for reporting recommendations to an individual, as used in an embodiment. The user interface may be displayed, for example, at block 1405 of FIG. 14, block 1506 of FIG. 15, block 1604 of FIG. 16, and/or block 1704 of FIG. 17. In various embodiments, additional blocks may be included, some blocks may be removed, and/or blocks may be connected or arranged differently from what is shown.

Interface element 1801 displays attributes of the individual and enables the individual to adjust those attributes. The interface element may be similar to interface element 901 of FIG. 9. Interface element 1802 may present similar options for adjusting attributes, in this case with respect to a potential partner. The inputs from interface elements 1801 and 1802 may be provided as inputs to the processes of generating recommendations. Alternatively to providing attributes using interface element 1802, attributes for the desired partner may be determined by the individual selecting a potential partner using interface element 1803. The individual may also request that the system identify recommendations that would increase the number of matches, using interface element 1804, which would invoke the process described with respect to FIG. 17, for example.

Interface element 1805 displays recommendations computed based on the individual's provided attributes. The recommendations may include text, numeric information, graphics, charts, the like. The user interface may identify particular recommendations, such as stronger recommendations, by sorting them, by highlighting them, by presenting them in a different font and/or size, by displaying numerical weights, by displaying a graphical indication of numerical weights, and the like. Alternately, the user interface may select one recommendation to present, or present multiple recommendations without indications of strength.

The interface may additionally or alternately provide recommendations based on the calculations. For example, interface element 1806 provides a list of suggested activities, which may be computed, for example, at block 1404 of FIG. 14. In an embodiment, the interface may provide direct links for the individual to participate in one or more of the suggested activities. Interface element 1807 displays an individual, such as a celebrity, that the system determines the individual should emulate in order to improve the individual's attributes along the lines of the recommendations.

Figure 19:
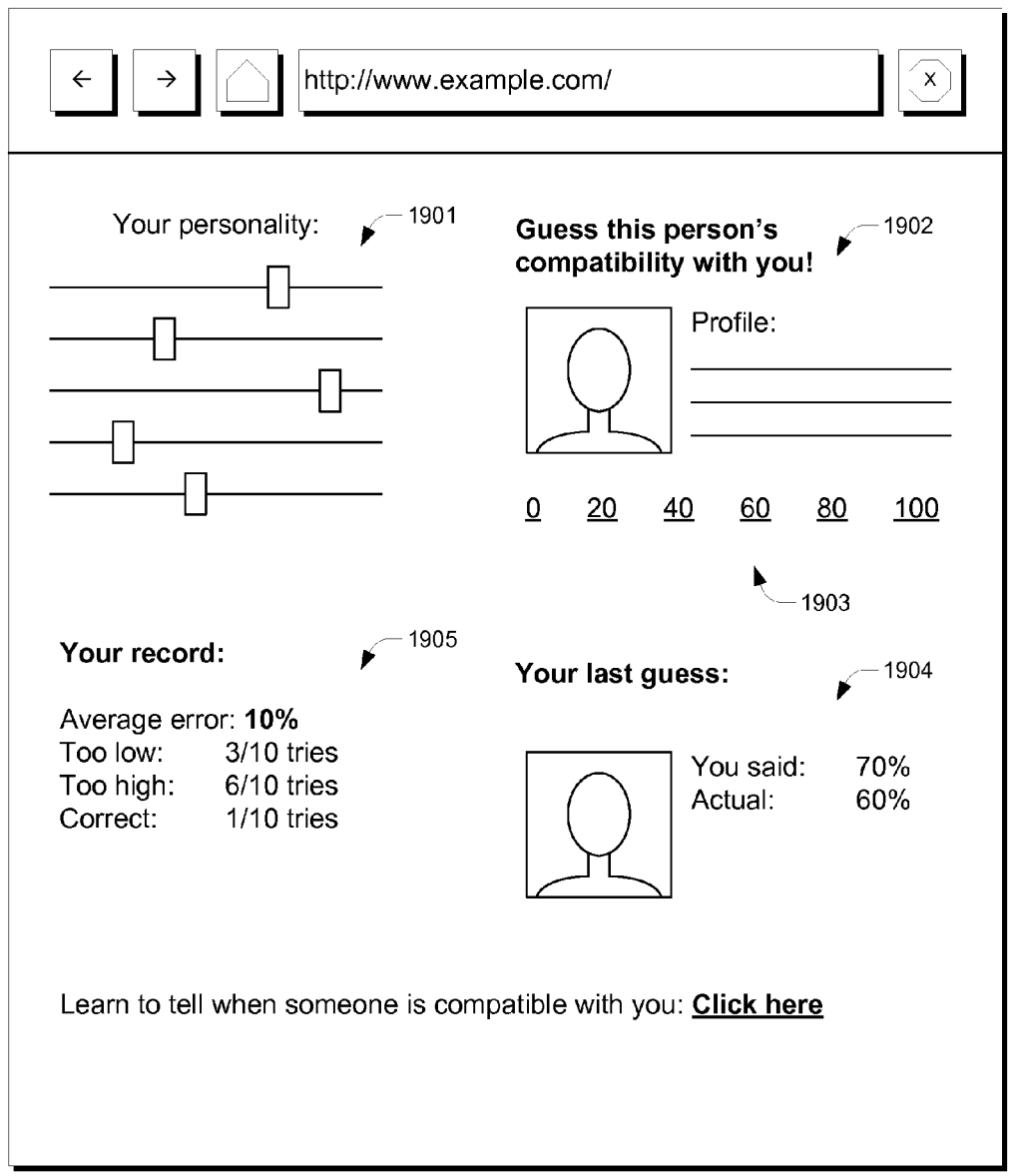
FIG. 19 is a user interface for a game based on the relationship satisfaction model, as used in an embodiment.

FIG. 19 is a user interface for a game based on the relationship satisfaction model, as used in an embodiment. In this game, the individual provides personality attributes and is then prompted to guess the compatibility of various potential partners with the individual. Such a game may be useful, for example, in improving the individual's ability to assess compatibility with others. In various embodiments, additional blocks may be included, some blocks may be removed, and/or blocks may be connected or arranged differently from what is shown.

Interface element 1901 enables the individual to view and/or provide personality attributes. The interface element may be similar to that described with respect to interface element 901 of FIG. 9. A selected profile of a potential partner is displayed at interface element 1902. The profile information may include a name, photograph, personal statement, and/or other information about the selected potential partner. In an embodiment, the potential partner is selected randomly. In an embodiment, the potential partner is selected from a list of potential partners that have a certain range of compatibility scores with the individual.

The individual may attempt to guess the compatibility with the potential partner using interface element 1903. The individual's guess may then be compared with the system's predicted compatibility score and subsequently displayed to the individual. This is shown in interface element 1904, which displays the individual's last guess and actual compatibility with the previously displayed potential partner. The user interface may further keep a running tally of the individual's success, such as that shown at interface element 1905. As described previously, particular numerical values may be not displayed and kept confidential, in some embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and tasks described herein may be performed and fully automated by a computer system. The computer system may, in some cases, include multiple distinct computers or computing devices (for example, physical servers, workstations, storage arrays, and so forth) that electronically communicate and interoperate over a network to perform the described functions. Each such computing device typically includes a processor (or multiple processors) that executes program instructions or modules stored in a memory or other computer-readable storage medium. Where the system includes multiple computing devices, these devices may, but need not, be co-located. The results of the disclosed methods and tasks may be persistently stored by transforming physical storage devices, such as solid state memory chips and/or magnetic disks, into a different state.

All of the methods and processes described above may be embodied in, and fully automated via, software code modules executed by one or more general purpose computers. The code modules may be stored in any type of computer-readable medium or other computer storage device. Some or all of the methods may alternatively be embodied in specialized computer hardware. The results of the disclosed methods can be stored in any type of computer data repository, such as relational databases and flat file systems that use magnetic disk storage and/or solid state RAM.

Many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being re-defined herein to be restricted to including any specific characteristics of the features or aspects of the invention with which that terminology is associated.

What is claimed is:

1. A method of making personality-related recommendations to an entity, the method being performed by a computer system comprising at least one computer processor, the method comprising:

receiving indications of personality attributes of an entity;

acquiring indications of personality attributes of a desired partner of the entity;

applying a mathematical model to the personality attributes of the entity and the personality attributes of the desired partner of the entity, the mathematical model calculating one or more recommended changes to the personality attributes of the entity to increase a predicted relationship satisfaction score between the entity and the desired partner, and the mathematical model comprising at least one numerical operation on at least one of the personality attributes of the entity, at least one of the personality attributes of the desired partner, and at least one statistical interaction term that reflects a synergistic and/or antagonistic relationship between the at least one of the personality attributes of the entity and the at least one of the personality attributes of the desired partner, wherein the at least one numerical operation comprises at least one summation operation and the at least one summation operation comprises a summation operation in the form of equation (1)

$$\sum_{y=1}^{n} \sum_{z=1}^{n} e_{yz} i_y p_z \qquad (1)$$

and n represents a discrete number of personality attributes, $i_y$ represents the personality attribute y of n for the entity, $p_z$ represents the personality attribute z of n for the desired partner, and $e_{yz}$ represents the statistical interaction term that reflects a synergistic and/or antagonistic relationship between the personality attribute y of n for the entity and the personality attribute z of n for the desired partner;

selecting a recommended action from a database of recommended actions, based at least in part on the recommended changes to the personality attributes of the entity; and transmitting an indication of the recommended action.

2. The method of claim 1, wherein acquiring indications of the personality attributes of the desired partner comprises:
receiving a selection of a partner; and
retrieving, from computer-readable data storage, personality attributes associated with the selected partner.

3. The method of claim 2, wherein the desired partner is a user having an account on the computer system.

4. The method of claim 2, wherein the desired partner is not a user having an account on the computer system.

5. The method of claim 1, wherein the recommended action is one or more of the recommended changes to the personality attributes of the entity.

6. The method of claim 1, wherein the recommended action is an activity that, by being performed by the individual, will bring about at least one of the recommended changes to the personality attributes of the entity.

7. The method of claim 1, wherein the mathematical model comprises a plurality of partial derivative functions based on a base model, the base model being configured to assess a relationship satisfaction score based on personality attribute inputs.

8. The method of claim 1, wherein transmitting the indication of the recommended action comprises transmitting web page data to a client computing device.

9. The method of claim 1, further comprising:
receiving proposed modifications to the personality attributes of the entity or the personality attributes of the individual;
reapplying the mathematical model with the proposed modifications; and
transmitting a real-time update to the indication of the recommended action.

10. A computer system configured to process personality-related data, the computer system comprising:
computer-readable storage having stored thereon a plurality of modules implemented as executable instructions;
one or more processors configured to execute instructions on the computer-readable storage;
an attribute acquisition module configured to acquire personality attributes of a first entity and personality attributes of a second entity;
a calculation module configured to apply a mathematical model to the personality attributes of the first entity and the personality attributes of the second entity, the mathematical model calculating one or more recommended changes to the personality attributes of the first entity to increase a predicted relationship satisfaction score between the first entity and the second entity, and the mathematical model comprising at least one numerical operation on at least one of the personality attributes of the first entity, at least one of the personality attributes of the second entity, and at least one statistical interaction term that reflects a synergistic and/or antagonistic relationship between the at least one of the personality attributes of the first entity and the at least one of the personality attributes of the second entity, wherein the at least one numerical operation comprises at least one summation operation and the at least one summation operation comprises a summation operation in the form of equation (1)

$$\sum_{y=1}^{n}\sum_{z=1}^{n} e_{yz} i_y p_z \qquad (1)$$

and n represents a discrete number of personality attributes,
$i_y$ represents the personality attribute y of n for the first entity,
$p_z$ represents the personality attribute z of n for the second entity, and
$e_{yz}$ represents the statistical interaction term that reflects a synergistic and/or antagonistic relationship between the personality attribute y of n for the first entity and the personality attribute z of n for the second entity; and
a recommendation module configured to generate a recommendation based at least in part on the recommended changes to the personality attributes of the first entity.

11. The computer system of claim 10, further comprising an proposed partner module configured to calculate personality attributes of a proposed partner for the first entity by applying a second mathematical model to the personality attributes of the first entity.

12. The computer system of claim 11, wherein the second mathematical model is configured to operate by:
applying the personality attributes of the first entity to a base model configured to assess a relationship satisfaction score based on personality attribute inputs of the first entity and the second entity; and
executing an algorithm to increase the relationship satisfaction score assessed by the base model, by varying values for the personality attributes of the second entity.

13. The computer system of claim 11, further comprising a matching module configured to identify one or more matching entities for the first entity, based on an application of a third mathematical model to the personality attributes of the first entity and personality attributes of the respective matched entities.

14. The computer system of claim 10, further comprising a user interface module configured to transmit web page data identifying the generated recommendation.

15. The computer system of claim 10, wherein the one or more processors are distributed across a plurality of computing devices connected via a network.

16. A non-transitory computer-readable medium having stored thereon a plurality of executable instructions configured to cause one or more processors to perform operations comprising:
receiving indications of personality attributes of an entity;
acquiring indications of personality attributes of a desired partner of the entity;
applying a mathematical model to the personality attributes of the entity and the personality attributes of the desired partner of the entity, the mathematical model calculating one or more recommended changes to the personality attributes of the entity to increase a predicted relationship satisfaction score between the entity and the desired partner, and the mathematical model comprising at least one numerical operation on at least one of the personality attributes of the entity, at least one of the personality attributes of the desired partner, and at least one statistical interaction term that reflects a synergistic and/or antagonistic relationship between the at least one of the personality attributes of the entity and the at least one of the personality attributes of the desired partner, wherein the at least one numerical operation comprises at least one summation operation and the at least one summation operation comprises a summation operation in the form of equation (1)

$$\sum_{y=1}^{n}\sum_{z=1}^{n} e_{yz} i_y p_z \quad (1)$$

and n represents a discrete number of personality attributes, $i_y$ represents the personality attribute y of n for the entity, $p_z$ resents the personality attribute z of n for the desired partner, and $e_{yz}$ represents the statistical interaction term that reflects a synergistic and/or antagonistic relationship between the personality attribute y of n for the entity and the personality attribute z of n for the desired partner;

selecting a recommended action from a database of recommended actions, based at least in part on the recommended changes to the personality attributes of the entity; and transmitting an indication of the recommended action.

17. The non-transitory computer-readable medium of claim 16, in combination with computer hardware including one or more processors.

18. The method of claim 1, wherein the one of the personality attributes of the entity is different than the one of the personality attributes of the desired partner.

* * * * *